US012745900B2

(12) United States Patent
Shahmoon et al.

(10) Patent No.: US 12,745,900 B2
(45) Date of Patent: Sep. 29, 2026

(54) ILLUMINATION SOURCES FOR MULTICORE FIBER ENDOSCOPES

(71) Applicant: ZSQUARE LTD., Petah Tikva (IL)

(72) Inventors: Asaf Shahmoon, Petah-Tikva (IL); Zeev Zalevsky, Rosh ha'ayin (IL)

(73) Assignee: ZSQUARE LTD., Petah Tikva (IL)

( * ) Notice: Subject to any disclaimer, the term of this patent is extended or adjusted under 35 U.S.C. 154(b) by 209 days.

(21) Appl. No.: 18/383,558

(22) Filed: Oct. 25, 2023

(65) Prior Publication Data

US 2024/0049956 A1 Feb. 15, 2024

Related U.S. Application Data

(63) Continuation of application No. 16/558,226, filed on Sep. 2, 2019, now abandoned, which is a
(Continued)

(51) Int. Cl.
*A61B 1/00* (2006.01)
*A61B 1/07* (2006.01)
(Continued)

(52) U.S. Cl.
CPC ............ *A61B 1/07* (2013.01); *A61B 1/00096* (2013.01); *A61B 1/00167* (2013.01);
(Continued)

(58) Field of Classification Search
CPC ... A61B 1/07; A61B 1/00096; A61B 1/00167; A61B 1/0017
See application file for complete search history.

(56) References Cited

U.S. PATENT DOCUMENTS 3,889,662 A * 6/1975 Mitsui ................ A61B 1/00181 385/119
4,656,508 A 4/1987 Yokota
(Continued)

FOREIGN PATENT DOCUMENTS

CN 1416235 5/2003
CN 101178460 5/2008
(Continued)

OTHER PUBLICATIONS

Ilovitch et al. "Time multiplexing super resolution using a Barker-based array" optics letters, p[tical society of America, US , vol. 40 No. 2 , Jan. 15, 2015 , pp. 163-165.
(Continued)

*Primary Examiner* — Timothy J Neal
(74) *Attorney, Agent, or Firm* — PEARL COHEN LLP

(57) ABSTRACT

Endoscopes, multicore endoscope fibers and configuration and operation methods are provided. The fibers may have hundreds or thousands of cores and possibly incorporate working channel(s) and additional fibers. The fiber may be used at different optical configurations to capture images of tissue and objects at the distal tip and to enhance a wide range of optical characteristics of the images such as resolution, field of view, depth of field, wavelength ranges etc. Near-field imaging as well as far-field imaging may be implemented in the endoscopes and the respective optical features may be utilized to optimize imaging. Optical elements may be used at the distal fiber tip, or the distal fiber tip may be lens-less. Diagnostics and optical treatment feedback loops may be implemented and illumination may be adapted to yield full color images, depth estimation, enhanced field of views and/or depths of field, and additional diagnostic data.

16 Claims, 16 Drawing Sheets

Related U.S. Application Data continuation-in-part of application No. 15/387,805, filed on Dec. 22, 2016, now Pat. No. 10,398,294, which is a continuation of application No. 14/805,915, filed on Jul. 22, 2015, now Pat. No. 9,661,986.

(60) Provisional application No. 62/119,832, filed on Feb. 24, 2015, provisional application No. 62/028,346, filed on Jul. 24, 2014.

(51) Int. Cl.

| | |
|---|---|
| ***G02B 6/02*** | (2006.01) |
| ***G02B 23/24*** | (2006.01) |
| ***G02B 23/26*** | (2006.01) |
| ***G02B 27/00*** | (2006.01) |
| ***G02B 27/28*** | (2006.01) |
| ***G02B 27/48*** | (2006.01) |
| ***H04N 13/161*** | (2018.01) |
| ***H04N 13/254*** | (2018.01) |
| ***H04N 13/296*** | (2018.01) |
| ***H04N 23/50*** | (2023.01) |
| *G02B 6/06* | (2006.01) |

(52) U.S. Cl.

CPC ........ *A61B 1/0017* (2013.01); *G02B 6/02042* (2013.01); *G02B 23/2423* (2013.01); *G02B 23/2469* (2013.01); *G02B 23/26* (2013.01); *G02B 27/0075* (2013.01); *G02B 27/283* (2013.01); *G02B 27/48* (2013.01); *H04N 13/161* (2018.05); *H04N 13/254* (2018.05); *H04N 13/296* (2018.05); *H04N 23/50* (2023.01); *G02B 6/06* (2013.01); *H04N 23/555* (2023.01)

(56) References Cited

U.S. PATENT DOCUMENTS

| | | | |
|---|---|---|---|
| 4,768,858 | A | 9/1988 | Hussein |
| 5,127,079 | A | 6/1992 | Suzuki et al. |
| 5,980,454 | A | 11/1999 | Broome et al. |
| 6,747,781 | B2 | 6/2004 | Trisnadi |
| 7,704,206 | B2 | 4/2010 | Suzuki et al. |
| 7,738,180 | B2 | 6/2010 | Igarashi |
| 9,661,986 | B2 | 5/2017 | Shahmoon et al. |
| 2002/0027708 | A1 | 3/2002 | Lin |
| 2003/0100824 | A1 | 5/2003 | Warren et al. |
| 2003/0144594 | A1 | 7/2003 | Gellman |
| 2003/0165313 | A1 | 9/2003 | Broeng et al. |
| 2004/0247268 | A1 | 12/2004 | Ishihara et al. |
| 2005/0027164 | A1 | 2/2005 | Barbato et al. |
| 2005/0043636 | A1 | 2/2005 | Gaeta et al. |
| 2007/0128749 | A1 | 6/2007 | Van Eijkelenborg et al. |
| 2007/0177009 | A1 * | 8/2007 | Bayer .................. A61B 1/0125 348/65 |
| 2008/0033301 | A1 | 2/2008 | DellaVecchia et al. |
| 2008/0058629 | A1 | 3/2008 | Seibel et al. |
| 2008/0107386 | A1 | 5/2008 | Kudou et al. |
| 2008/0137363 | A1 | 6/2008 | Harris |
| 2009/0002794 | A1 | 1/2009 | Weir et al. |
| 2009/0137893 | A1 | 5/2009 | Seibel et al. |
| 2009/0244260 | A1 | 10/2009 | Takahashi et al. |
| 2010/0274082 | A1 | 10/2010 | Iguchi et al. |
| 2011/0137126 | A1 | 6/2011 | French et al. |
| 2011/0301414 | A1 | 12/2011 | Hotto et al. |
| 2012/0093401 | A1 | 4/2012 | Tsunematsu |
| 2012/0215065 | A1 | 8/2012 | Mukherjee |
| 2013/0156389 | A1 | 6/2013 | Shinji et al. |
| 2013/0171667 | A1 | 7/2013 | Unnimadhava Kurup Soudamini Amma et al. |
| 2013/0278740 | A1 | 10/2013 | Zalevsky et al. |
| 2014/0024951 | A1 | 1/2014 | Herzlinget et al. |
| 2014/0055582 | A1 | 2/2014 | Demers et al. |
| 2015/0015879 | A1 | 1/2015 | Papadopoulos et al. |
| 2015/0208144 | A1 | 7/2015 | Holmes |
| 2016/0022119 | A1 | 1/2016 | Shahmoon et al. |
| 2016/0365697 | A1 | 12/2016 | Hori et al. |

FOREIGN PATENT DOCUMENTS

| | | |
|---|---|---|
| CN | 101861515 | 10/2008 |
| CN | 101833131 | 9/2010 |
| CN | 102221743 | 4/2011 |
| CN | 102203648 | 9/2011 |
| CN | 201974557 | 9/2011 |
| CN | 102971652 | 3/2013 |
| CN | 103105681 | 5/2013 |
| CN | 103515018 | 4/2017 |
| EP | 1 918 743 | 5/2008 |
| EP | 3100669 | 12/2016 |
| JP | S62-080605 | 11/1985 |
| JP | H04-340516 | 11/1992 |
| JP | H08-248238 | 9/1996 |
| JP | 2003-05499 | 2/2003 |
| JP | 2004-317437 | 11/2004 |
| JP | 2008-116745 | 5/2008 |
| JP | 2000-023907 | 1/2009 |
| JP | 2012-253156 | 11/2010 |
| JP | 2011-527218 | 10/2011 |
| JP | 2014-052902 | 3/2013 |
| WO | WO 2005/119328 | 12/2005 |
| WO | WO 2011/155444 | 8/2013 |
| WO | WO 2012/132750 | 7/2014 |

OTHER PUBLICATIONS

Ilovitch et al. "Time Multiplexing super resolution using a 2D Barker-based array" Progress in Biomedical Optics and Imaging, SPIE—International society for optical Engineering, Bellingham, WA, US, vol. 9716, Mar. 9, 2016, pp. 971601-971601.

Fortin et al., Evaluation of the microscanning process, 1994, pp. 1-9.

Anonymous, Modulus of Elasticity—Young Modulus for some common materials, Jun. 26, 2014, XP055453809, Retrieved from the Internet: URL:hhttps://web.archive.org/web/20140626005910/https://www.engineeringtollbox.com/young-modulus-d_417.html, [retrieved on Feb. 23, 2018] p. 2.

Japanese Office Action for JP Application No. 2017-524140 dated May 14, 2019.

International Search Report for PCT application No. PCT/IL2017/051372 dated Apr. 15, 2018.

Extended Search report of European Patent Application No. 15824210.7 mailed Jun. 3, 2018.

Extended Search report of European Patent Application No. 17883995.7 mailed Jun. 30, 2020.

* cited by examiner

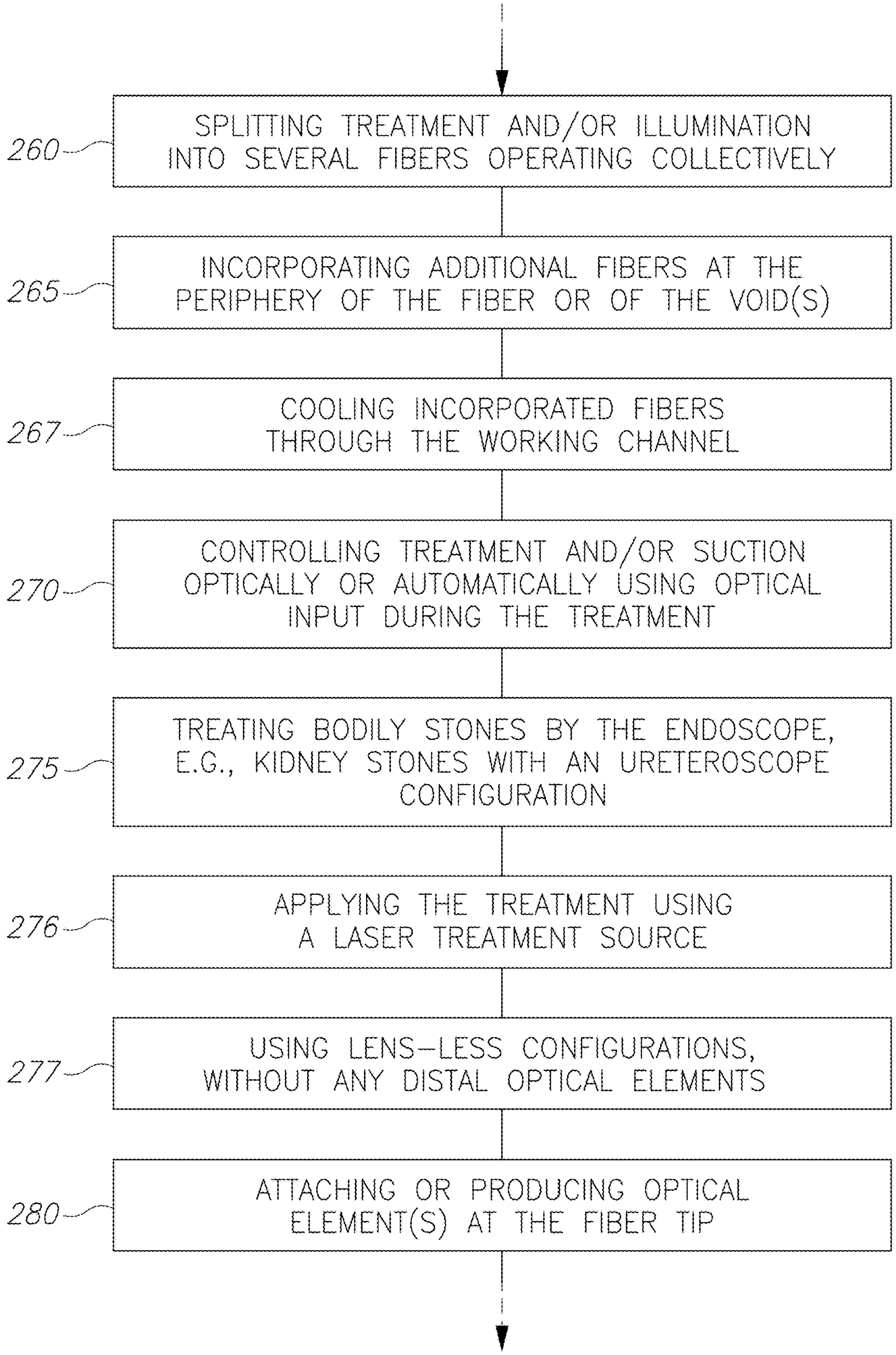
Figure 7 (cont. 1)

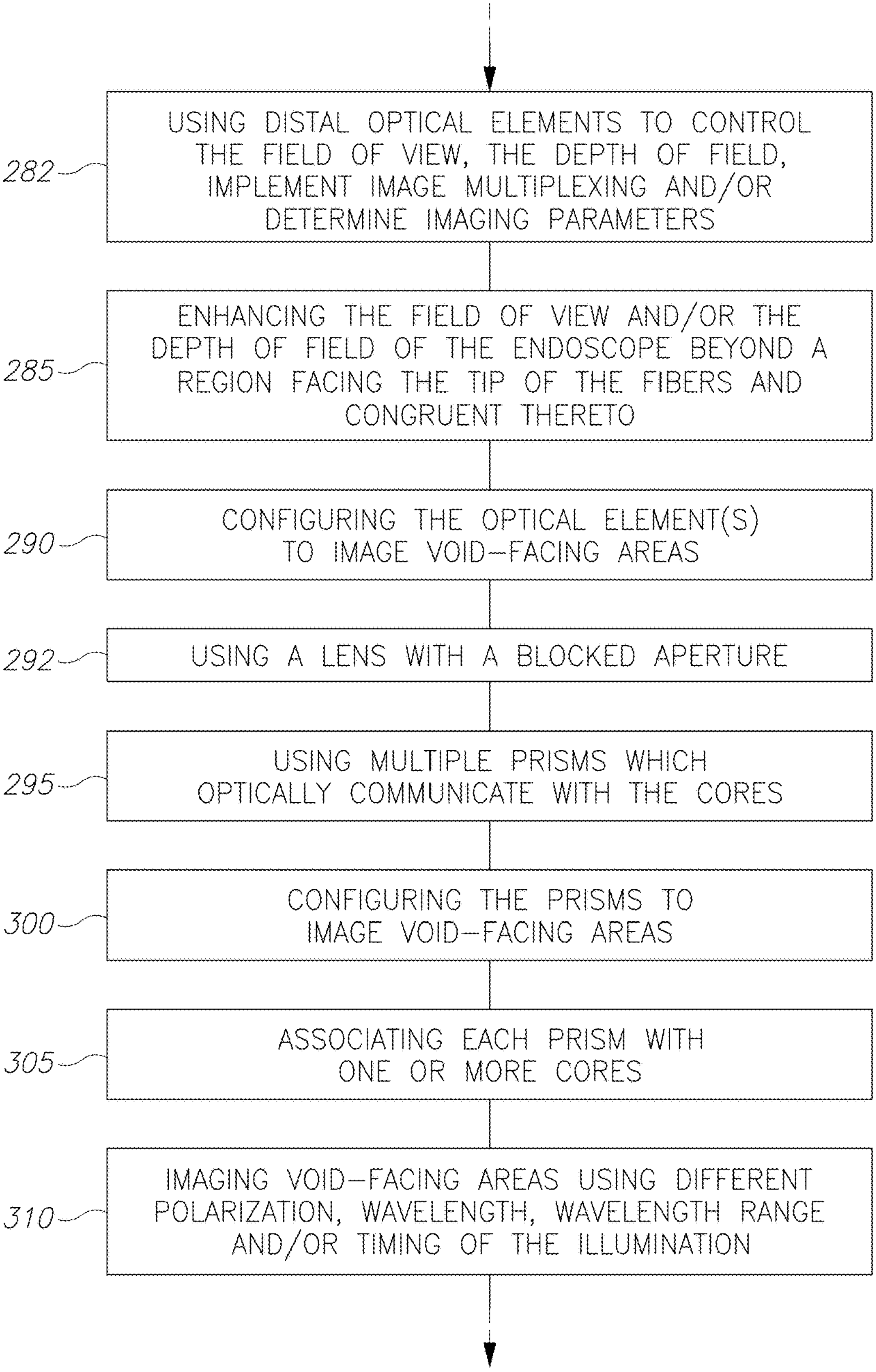
Figure 7 (cont. 2)

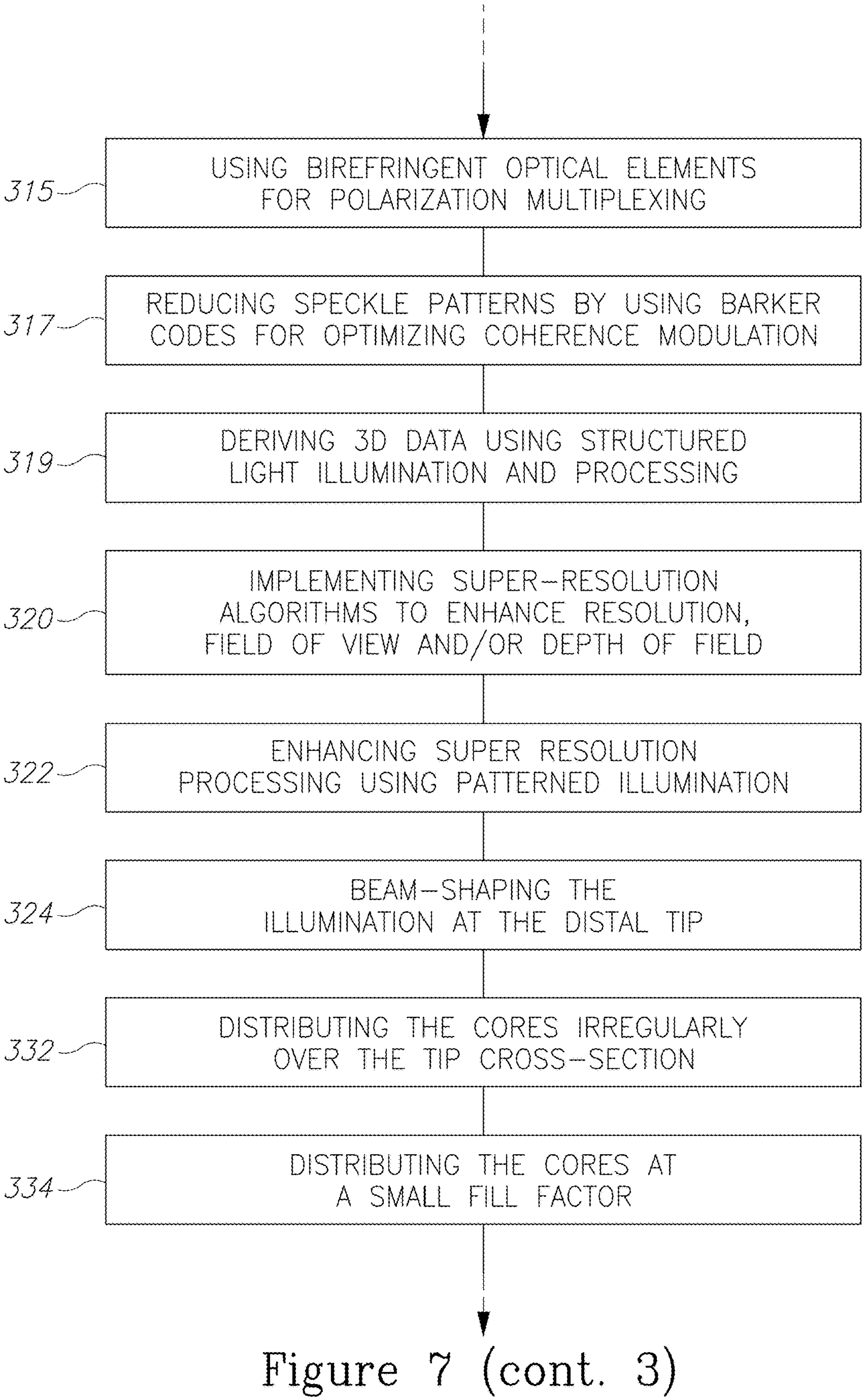
Figure 7 (cont. 3)

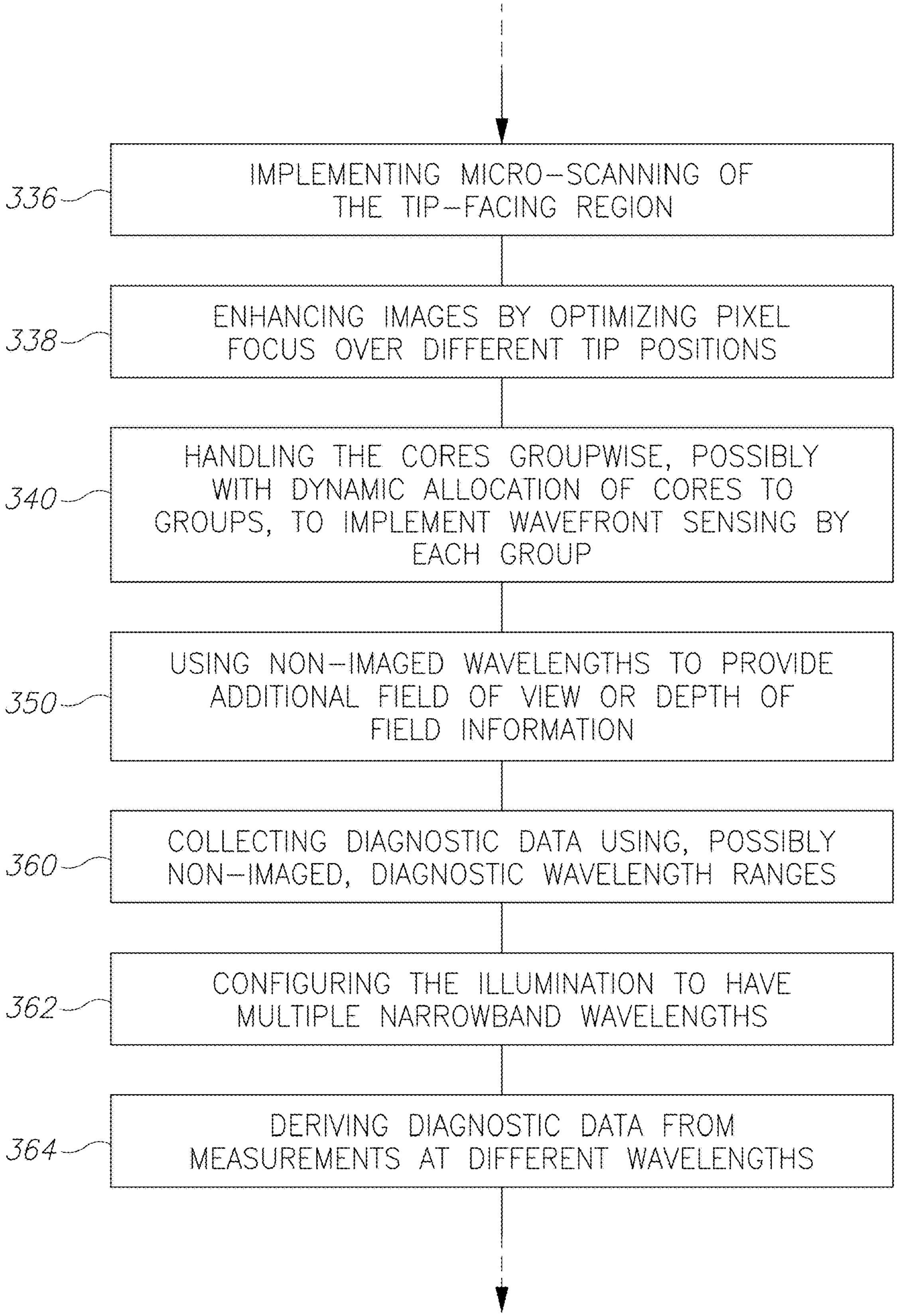
Figure 7 (cont. 4)

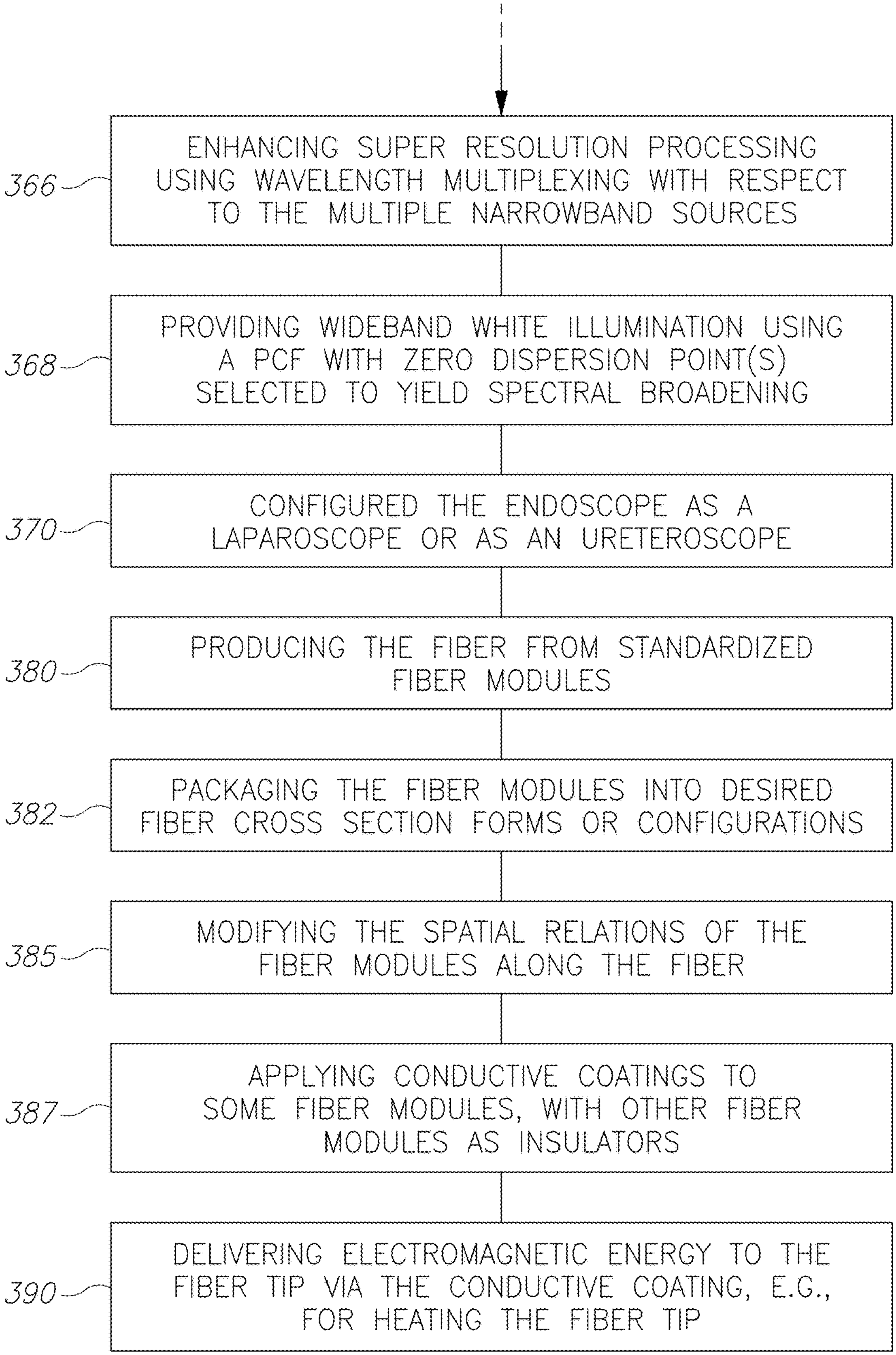
Figure 7 (cont. 5)

ILLUMINATION SOURCES FOR MULTICORE FIBER ENDOSCOPES

CROSS REFERENCE TO RELATED APPLICATIONS

This application is a continuation of U.S. patent application Ser. No. 16/588,226, filed Sep. 2, 2019, which is a continuation of U.S. patent application Ser. No. 15/387,805 filed on Dec. 22, 2016, which is a continuation in part of U.S. patent application Ser. No. 14/805,915 filed on Jul. 22, 2015 which is now U.S. Pat. No. 9,661,986 registered on May 30, 2017, which claims priority under 35 U.S.C. § 119 to U.S. Provisional Patent Application No. 62/028,346 filed on Jul. 24, 2014 and to U.S. Provisional Patent Application No. 62/119,832 filed on Feb. 24, 2015, all of which are incorporated herein by reference in their entireties.

BACKGROUND OF THE INVENTION

1. Technical Field

The present invention relates to the field of endoscopy, and more particularly, to multicore fiber endo scopes.

2. Discussion of Related Art

Endoscopes in various configurations allow efficient treatment of a range of medical problems, as well as means for manipulating different situations with limited access. Endo scope operations are challenging in that illumination, detection and treatment are confined to long and narrow operations modes. Fiber optics technology is a central enabler for such techniques, and fiber-based endoscope experience continuous improvements.

SUMMARY OF THE INVENTION

The following is a simplified summary providing an initial understanding of the invention. The summary does not necessarily identify key elements nor limit the scope of the invention, but merely serves as an introduction to the following description.

One aspect of the present invention provides an endoscope having a distal tip and a proximal tip, the endoscope comprising at least one multicore fiber module comprising at least one hundred cores distributed at a fill factor smaller than ¼, an illumination source coupled to the at least one multicore fiber module and configured to deliver illumination thereto, at least one optical element, in optical communication with the cores, at the distal tip, a detector, in optical communication with the cores, at the proximal tip, and a processor configured to receive images from the detector; wherein the endoscope is configured to implement super-resolved imaging by micro scanning over a pitch distance between the cores, and wherein the endoscope is configured to implement three dimensional sensing by handling the cores group-wise with respect to radiation delivered therethrough, and to at least one of: enhance, by configuring the at least one optical element, a field of view of the endoscope beyond a region facing the cores at the distal tip, and enhance, by configuring the at least one optical element, a depth of field of the endoscope beyond a region congruent to the distal tip.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

Figure 1B:
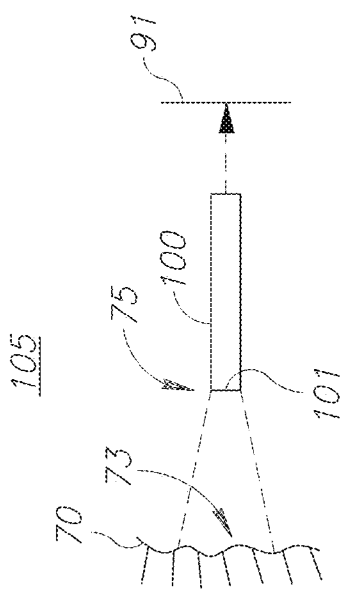
FIGS. 1A-1E are high level schematic illustrations of endoscope configurations according to some embodiments of the invention.

Prior to the detailed description being set forth, it may be helpful to set forth definitions of certain terms that will be used hereinafter.

The terms "distal" and "proximal" as used in this application refer to the ends of the endoscope. The end and associated parts of the endoscope which are far from the endoscope's interface (detector or eye) and close to the imaged tissue and to its surroundings is termed the distal end, while the end and associated parts of the endo scope which are close to the endoscope's interface and are remote from the imaged tissue, being typically outside the body is termed the proximal end. The term "reflected" as used in this application refers to a change in a direction of an illumination wavefront which impacts one or more imaged object or tissue. The term "reflection" is understood broadly as any radiation gathered by the fiber, irrespective of the source of the illumination which is reflected by the object(s) and/or tissue(s).

The term "near field imaging" as used in this application refers to the formation of an image (of imaged objects, tissues and/or their surroundings) at the distal end of the endoscope fiber, typically at the fiber's tip. The imaged is then typically transferred through the fiber to the detector, possibly through proximal optical elements. The term "near field imaging" may relate to different types of optical systems, including direct imaging without any optical elements between the imaged object or tissue and the fiber tip as well as to imaging through optical element(s) such as lenses.

The term "far field imaging" as used in this application refers to the formation of a Fourier transform of imaged objects, tissues and/or their surroundings at the distal end of the endoscope fiber (e.g., the distal end of the endoscope fiber is at the aperture or pupil plane of the optical system), typically at the fiber's tip. The image of the imaged objects, tissues and/or their surroundings may be formed at the proximal end of the endoscope fiber, typically at the fiber's proximal tip or directly on the detector, possibly through proximal optical elements. The term "far field imaging" may relate to different types of optical systems. In one example, "far field imaging" may be direct in the sense that no optical elements are used between the imaged object or tissue and the distal fiber tip, which delivers radiation entering the fiber along the fiber to the detector at the proximal end of the fiber. In another example, "far field imaging" may be carried out with optical elements positioned between the imaged object or tissue and the distal fiber tip, with the distal fiber tip being at least approximately at the Fourier plane (also termed aperture plane and pupil plane in different contexts) of the optical elements.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Endoscopes, multicore endoscope fibers and configuration and operation methods are provided. The fibers may have hundreds or thousands of cores and possibly incorporate working channel(s) and additional fibers. The fiber may be used at different optical configurations to capture images of tissue and objects at the distal tip and to enhance a wide range of optical characteristics of the images such as resolution, field of view, depth of field, wavelength ranges etc. Near-field imaging as well as far-field imaging may be implemented in the endoscopes and the respective optical features may be utilized to optimize imaging. Optical elements may be used at the distal fiber tip, or the distal fiber tip may be lens-less. Diagnostics and optical treatment feedback loops may be implemented and illumination may be adapted to yield full color images, depth estimation, enhanced field of view and/or depth of field and additional diagnostic data, as disclosed below.

In the following, various embodiments of multicore endoscope fibers are disclosed. The described embodiments are roughly and not exclusively described in groups relating to the following traits. Certain endoscope embodiments may implement far field imaging (see FIG. 1A below), e.g., have the image formed at the proximal end of the endo scope fiber, while certain endoscope embodiments may implement near field imaging (see FIG. 1B below), e.g., have the image formed at the distal end of the endoscope fiber. Both far field and near field implementations, may have distal optical elements between the imaged objects or tissues and the distal fiber tip (see FIG. 1C below), or may operate without such distal optical elements (see FIG. 1D below). Each of the four combinations (far field with or without distal optical elements and near field with or without distal optical elements) has different features, advantages and disadvantages as exemplified in Table 1, and may be selected according to specific implementation scenarios. Alternation of the combination may be carried out between applications or in real time, to combine advantages of different configuration types. It is further noted that endoscopes may be designed to have several combinations, e.g., a part of the fiber face (or certain fiber modules) having distal optics for imaging far objects and another part of the fiber face (or other fiber modules) lacking distal optics for microscopic imaging.

TABLE 1

Characteristics of different embodiments

| | Far-field imaging | Near-field imaging |
|---|---|---|
| Distal fiber tip With distal optics | Fourier plane Larger region of interest | Image plane Larger field of view, Image multiplexing, larger energetic efficiency |
| | Larger field of view which may include working channel without compromising (central) regions in the field of view | |
| No distal optics | Wavefront sensing, optical zooming | Auto focus and optical zooming capabilities |
| | Simpler production and fiber management | |

Certain embodiments comprise lens-less embodiments in which the distal fiber tip lacks optical elements. Lens-less embodiments may implement either far-field or near-field imaging, and may utilize structural features to enhance optical resolution, apply super-resolution methods and retrieve wavefront information while reducing crosstalk between the cores.

Endoscope embodiments may have full tip cross sections or have working channel(s) within the imaging fiber characterized by different configurations and uses, integrating additional fibers etc., in which case the cores and optical elements may be configured to overcome the reduction of the field of view due to the incorporation of the working channel.

In the following, various configurations of the large number of cores in the fiber are disclosed, which provide solutions to various issues such as reducing crosstalk between the fibers, overcoming material losses, achieving enhanced resolution by different methods, providing required mechanical characteristics and optimizing the imaging performances of the endoscope fibers. The disclosed endoscopes may serve different purposes, e.g., may be designed as a laparoscope or an ureteroscope. It is noted that elements disclosed in the context of some of the embodiments are not necessarily limited to these embodiments but may be implemented within other embodiments as well.

FIGS. 1A-1E are high level schematic illustrations of endoscope configurations according to some embodiments of the invention. Proposed micro endoscope 105 is constructed from large plurality of cores (e.g. one hundred cores or more, hundreds of cores, thousands of cores, in certain embodiments tens or hundreds of thousand cores per fiber or fiber module, reaching over a million cores in certain fiber endoscopes), each responsible for transferring a single or a large number of spatial degrees of freedom out of which at the output, proximal end (the one external to the patient body), a high resolution color image may be constructed. Multi-core fiber 100 exhibits a high degree of flexibility in its optical design, as exemplified below, which may be utilized and adapted for specific applications, for example for ureteroscopes with a large working channel and a small external diameter or for laparoscopes with a very high resolution obtained at a small external diameter.

Endoscope 105 may be configured to carry out far-field imaging, near-field imaging or a combination of far-field imaging and near-field imaging. Irrespectively of the imaging mode, endo scope 105 may be configured to have one or more optical elements 140 at a distal tip 101 of fiber 100 or have no optical elements between tip 101 and imaged tissue(s) or object(s) 70. Certain embodiments may comprise removable or reconfigurable optical elements 140 at tip 101 and/or optical elements 140 affecting only parts of the surface of distal tip 101 (e.g., sub-group(s) of the cores).

Certain embodiments comprise endo scopes 105 having a plurality of fibers 100, grouped together, each having at least one hundred cores distributed at a fill factor smaller than ¼, or even smaller than ⅑, at least one photonic illumination fiber, and at least one optical element at a distal tip of fibers 100, which may be configured to enhance a field of view and/or a depth of field of endoscope 105 beyond a region facing a tip of fibers 100 and congruent thereto (see details below). Endoscope 105 may be further configured to implement three dimensional sensing by handling the cores groupwise with respect to radiation delivered therethrough (see details below). Endoscope 105 may be further configured to super-resolved imaging by micro scanning over a pitch distance between the cores (see details below). Endoscope 105 may be configured to comprise a LED (light emitting diode) light source located at distal tip 101 as the illumination source.

Figure 1D:
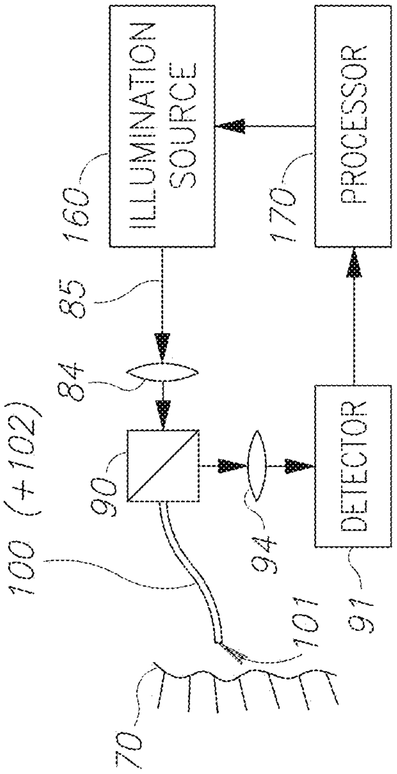
Figure 1A:
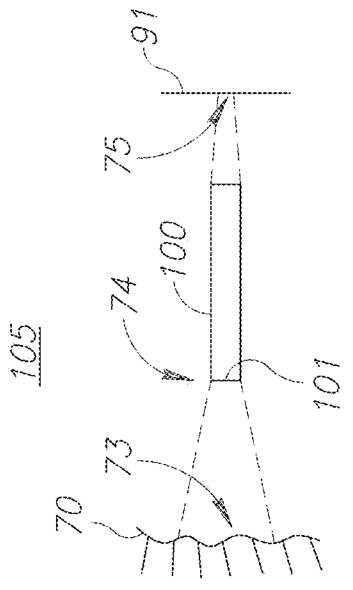

FIG. 1A schematically illustrates far-field imaging, in which an image 73 (indicating any kind of electromagnetic signal reflected from tissue or object 70) is delivered through tip 101 and fiber 100 to yield image 75 on detector 91. Tip 101 may be a Fourier plane (also termed aperture plane or pupil plane) at which the Fourier transform 74 of image 73 enters fiber 100. It is noted that the Fourier plane may be located anywhere along fiber 100 as well as distally or proximally to fiber 100, in different embodiments of the invention, and be optically transformed to image 75 on detector 91. Alternatively or complementary, Fourier image 74 or derivatives thereof may be measured at detector 91, and/or manipulated to enhance imaging parameters such as resolution, field of view and depth of focus, as non-limiting examples. Optical elements may be introduced distally or proximally to fiber 100 to modify or manipulate the radiation entering tip 101 and the radiation falling on detector 91, respectively.

FIG. 1B schematically illustrates near-field imaging, in which image 73 yields image 75 at fiber tip 101. Image 75 is then delivered, possibly through optical elements, to detector 91 through fiber 100. It is noted that image 75 may be formed within fiber 100 and not necessarily exactly at tip 101. Image 75 delivered via fiber 100 may be measured at detector 91, and/or manipulated to enhance imaging parameters such as resolution, field of view and depth of focus, as non-limiting examples. Optical elements may be introduced distally or proximally to fiber 100 to modify or manipulate the radiation entering tip 101 and the radiation falling on detector 91, respectively.

Figure 1C:
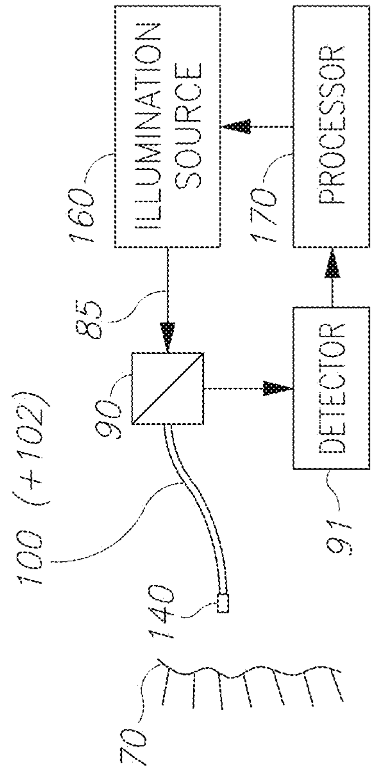

FIG. 1C schematically illustrates optical configurations having one or more optical element(s) 140 at the distal end of fiber 100, at proximity to imaged tissue 70. Optical element(s) 140 may be attached to tip 101 or may be somewhat distally removed from tip 101 (e.g., held by spacers at a distance therefrom). Each optical element 140 may be in optical communication with a respective core or a respective group of cores. Proximally, illumination 85 is delivered to fiber 100 by an illumination source 160, and reflected illumination (e.g., in far-field, in near-field or in an intermediate plane) is directed from the cores to a detector 91, e.g., via a beam splitter 90. Proximal optical elements may be set and used to manipulate illumination 85 and the reflected illumination, as symbolized below (FIG. 1D) by lenses 84, 94 respectively. One or more processor(s) 170 may be configured to control the illumination and/or process the detected illumination, as well as control illumination and image beams in case there are controllable elements in the optical path.

FIG. 1D schematically illustrates optical configurations having no optical element(s) (also termed below "lens-less" configurations) at the distal end of fiber 100, so that fiber tip 101 is used directly to deliver and receive illumination to and from imaged tissue 70. Illumination 85 is delivered to fiber 100 proximally, e.g., via an optical element 84 such as a lens, and reflected illumination is directed to detector 91 via another optical element 94, e.g., a lens. One or more processor(s) 170 may be configured to control the illumination and/or process the detected illumination, as well as control illumination and image beams in case there are controllable elements in the optical path. In certain embodiments, lens-less configurations may be configured to generate image at "contact mode", e.g., with close proximity of the fiber tip to the examined tissue, to yield microscopic resolution determined by the sizes of the cores.

In certain embodiments, proximal optical elements 94 (and possibly optical elements 84 too) may be variable and be used to adjust the plane and depth of focus of captured images in far-field imaging configurations, especially in lens-less configurations.

Figure 1E:
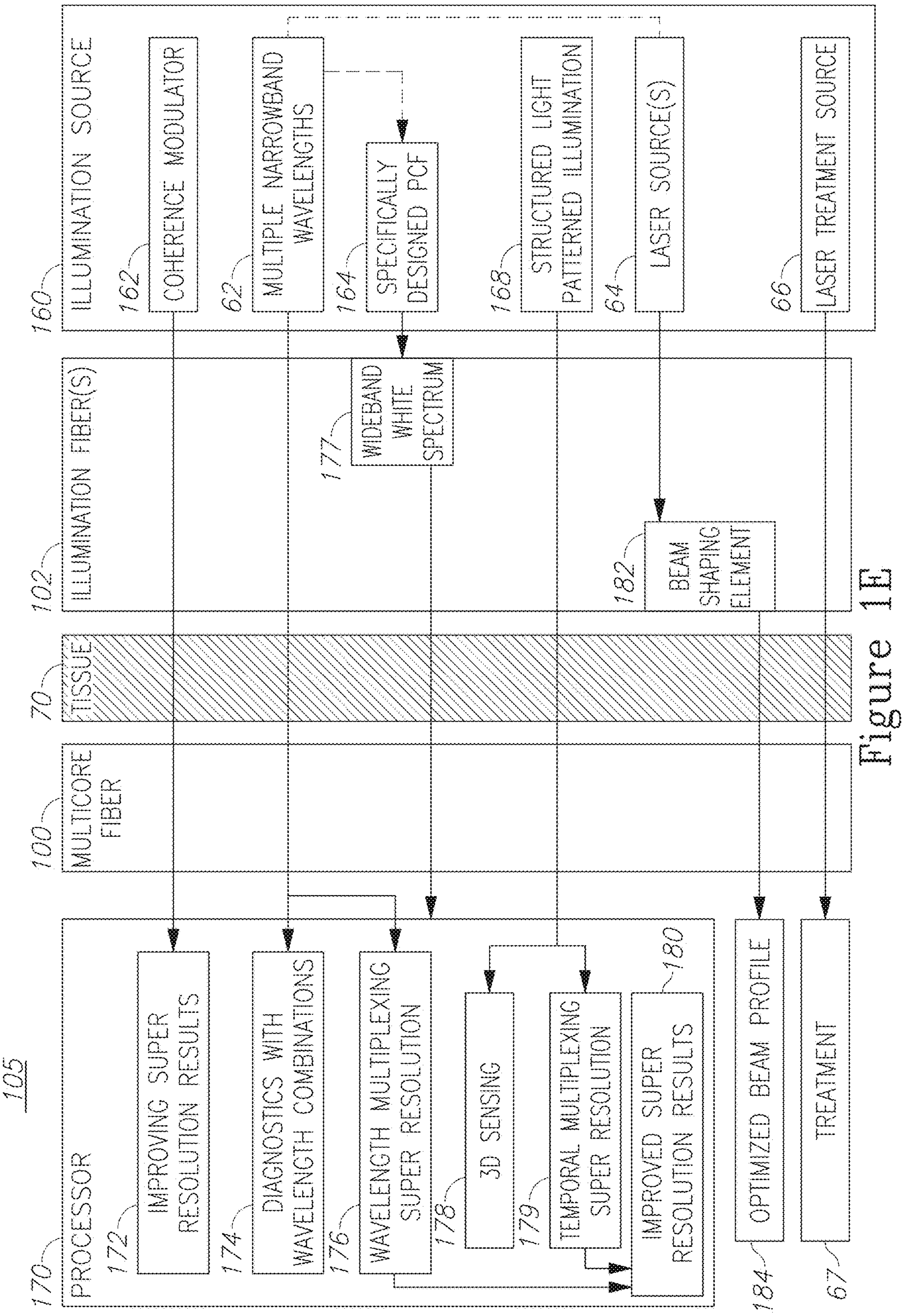

FIG. 1E is a high level schematic block diagram illustrating endoscope configurations according to some embodiments of the invention. Various embodiments are illustrated, which may be stand-alone embodiments or be implemented in any combination thereof. In particular, various embodiments of illumination source 160 and of configurations of processor 170 are presented, which may be used to improve the spatial resolution, in particular when using super resolution algorithms, improve the beam quality and/or enhance the functionality of endoscope 105 with respect to its medical uses and image quality. Embodiments illustrated in FIG. 1E may be applied to any embodiment of endoscope 105 described herein. It is noted that illumination source 160 may be configured to deliver illumination 85 through one or more dedicated illumination fiber(s) 102 and/or through multicore fiber 100. For example, illumination fiber(s) 102 may be multimode fiber(s), possibly made of glass fiber, which are associated with multicore fiber 100, e.g., attached thereto or positioned in a cavity in multicore fiber 100. Alternatively or complementarily, illumination fiber(s) 102 may be positioned to illuminate tissue 70 in any other spatial relation to multicore fiber 100, possibly in no mechanical association therewith. In certain embodiments, one or more of illumination fiber(s) 102 may be single mode fibers. It is noted that the spatial relation between illumination fiber(s) 102 and multicore fiber 100 may be configured to have multicore fiber 100 receive radiation (illuminated by illumination fiber(s) 102) which is reflected off tissue 70 and/or transmitted through tissue 70, depending on specific use conditions.

In some embodiments, illumination source 160 may comprise a coherence modulator 162 configured to enable processor 170 to implement algorithms for improving super resolution results 172. For example, coherence modulator 162 may be configured to use a coherence modulation of illumination 85 that reduces speckle patterns by modulating the coherence using Barker codes rather than random prior art modulation. Advantageously, using Barker codes may reduce the required number of modulation steps for a given reduction of speckle patterns due to the orthogonality between the Barker codes and other characteristics of their definition. Specific Barker codes may be selected to optimize their application.

In some embodiments, illumination source 160 may comprise multiple narrowband wavelengths 62 (e.g., narrowband spectral ranges around specified wavelengths) which may be used in processors 170 configured to provide diagnostics using one or more wavelength combinations 174, discussed below in more detail, and/or configured to implement wavelength multiplexing super resolution 176 by changing the ratios between specific wavelengths (e.g., between narrowband red, green and blue sources 62)—to achieve improved super resolution results 180.

In some embodiments, illumination source 160 may comprise one or more photonic crystal fiber (PCF) 164 configured to deliver wideband white spectrum 177 into dedicated illumination fiber(s) 120 and/or multicore fiber 100, e.g., utilizing supercontinuum effects (bandwidth broadening due to nonlinear effects) to provide white illumination of tissues that is closer to natural wideband illumination than illumination with narrowband red, green and blue sources 62 which are delivered to PCF 164. PCF 164 may be coupled to one or more narrowband sources 62 and designed to have zero dispersion point(s) at the wavelengths of source(s) 62 to yield spectral broadening. Using several multiple narrowband wavelengths 62 may provide wideband white spectrum 177 through a combination and merging of the broadened spectra of source(s) 62. Improved white spectrum 177 may be advantageous to provide truer imaging colors be endoscope 105.

In some embodiments, illumination source 160 may comprise structured light patterned illumination 168, which may be used in processor 170 configured to provide 3D sensing 178 by analyzing the illuminated patterns on the tissue and/or improved super resolution results 180 by utilizing the parameters of the temporally changing spatially projected patterns of illumination 168 to implement temporal multiplexing super resolution 179.

In some embodiments, illumination source 160 may comprise one or more laser source(s) 64 (possibly narrowband sources 62) in illumination source 160 and at least one beam shaping element 182 at the distal end of multicore fiber 100 which is configured to generate an optimized beam profile 184 to improve illumination 85. For example, beam profile 184 may comprise a uniform illumination distribution in space or a rectangular uniform profile (top hat illumination distribution), which are advantageous with respect to prior art Gaussian illumination distribution with respect to various parameters of the resulting images. The coherence of laser source(s) 64 may be used to shape illumination beam 85 efficiently by beam shaping element 182. In some embodiments, at least one beam shaping element 182 may be set at the proximal end of multicore fiber 100.

In some embodiments, illumination source 160 may comprise one or more laser treatment source(s) 66 which are configured to apply a specified treatment 67 by endoscope 105, e.g., to a tissue. For example treatment 67 may be applied to kidney stones in endo scope 105 designed as an uretero scope, as described below in more details.

Figures 2A, 2B, 2C, 2D, 2E:
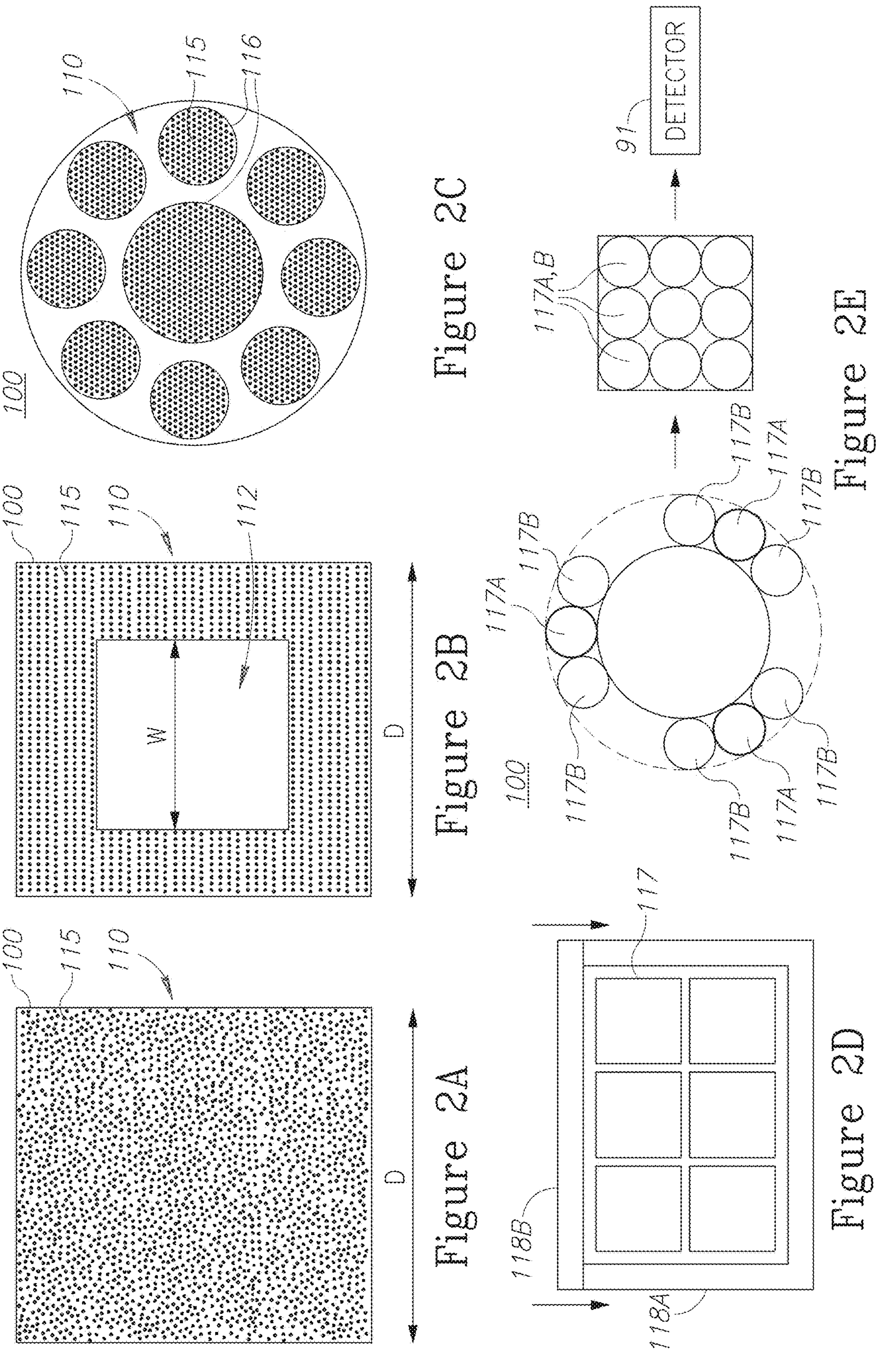
FIGS. 2A-2C are high level schematic illustrations of fiber cross sections having a large number of cores in their electromagnetic propagation region(s), according to some embodiments of the invention.
FIGS. 2D and 2E are high level schematic illustrations of fiber production by packing fiber modules, according to some embodiments of the invention.

FIGS. 2A-2C are high level schematic illustrations of fiber cross sections having a large number of cores 115 in their electromagnetic propagation region(s) 110, according to some embodiments of the invention. Fiber(s) 100 may comprise central or eccentric optical cores (110) and/or may have hollow, central or eccentric region(s) (112) that may be used for treatment such as energy delivery, suction, illumination, drug delivery etc. Illumination means (such as dedicated illumination fiber(s) 102), may be integrated in various ways within the multicore fibers 100. Selection of near-field or far-field configurations, as well as selection if and which optical elements 140 are inserted distally to the tip, may be carried out under consideration of the tradeoffs between the different applications (see e.g., Table 1 and other examples below). For example, considerations concerning production, use, optical characteristics and algorithmic parameters may be balanced differently at different embodiments to optimize endo scope 105 to a wide range of performance and device requirements.

Fiber 100 illustrated in FIG. 2A may have any form of cross section, e.g., square as illustrated in a non-limiting manner, round, hexagonal, elliptic etc. While FIG. 2A illustrates a solid cross section of fiber 100, FIG. 2B illustrates hollow endoscope having a void 112 within fiber 100 that may be used for different purposes as disclosed below (e.g., as a working channel for inserting a tool or carrying out suction, for incorporating additional fibers etc.). Fibers 100 may be square, round or have any other form, and void 112 may too have any shape and any position within fiber 100, void(s) 112 and fiber 100 may have any dimensions ($R_i$, $R_o$, D, W etc.), and voids may also be multiple (e.g., fiber 100 may enclose two or more voids), all designed according to requirements from the endoscope. FIG. 2C schematically illustrates multicore fiber 100 with cores 115 grouped into "super core" groups 116 that may be configured to sense wavefronts in lens-less configurations, as explained below.

Multicore fiber 100 may be made of biocompatible materials in case of medical uses, e.g., polymers such as PMMA (poly-methyl methacrylate) and PS (polystyrene) and may be flexible. Fiber 100 may also be made of non-compatible materials and be flexible or rigid in case of industrial uses. Fiber 100 may be configured to have a flexibility characterized by a Young's modulus smaller than 10 GPa and to be disposable. Fiber 100 may thus be more flexible than glass fiber (having a Young's modulus of about 65 GPa), and may reach PMMA flexibility (Young's modulus between 1.8 and 3.1 GPa) or higher flexibility.

Various embodiments compensate for the reduced transparency of polymer fibers with respect to glass fibers, using means such as fiber materials, configuration of cores and interspaces, number and sizes of cores, material modifications of different fiber parts, control over the number of propagation modes in cores 115, optical means such as lenses or prisms at either side of fiber 100 and their configuration, design and application of different types of illumination and algorithmic solutions, all of which are exemplified below in a non-limiting manner. The following disclosure also addresses ways to control cross talk between cores 115 (e.g., interaction effects between radiation propagating in adjacent cores 115) and ways to improve the information content and to enhance treatment-relevant information of the detected images.

Illumination may comprise coherent light or incoherent light, any spectral pattern (broad or narrow wavelength ranges, continuous or discrete ranged), polarized (in various patterns) or non-polarized light and different ranges in the visual or infrared ranges. Material differences between cores, interspaces and outer cladding may comprise different materials, using air cores or air interspaces, and doping any of the fiber regions to influence their refractive indices, as explained in more details below. It is noted that any of the embodiments presented below may be used in any of the other embodiments described herein, as long as they are compatible. Particularly, computational methods optical methods and fiber design considerations described in the context of any embodiment may be applied to other embodiments as well.

FIGS. 2D and 2E are high level schematic illustrations of fiber production by packing fiber modules, according to some embodiments of the invention. Multi-core fibers 100 may be produced using fiber modules or units 117. Each fiber module 117 is itself a multicore fiber, possibly configured to have uniform dimensions. Such embodiments are referred to as bundled fibers, and may bundle any number of fiber modules 117 in any configuration (e.g., 2×2 modules, 3×3 modules etc.). Fiber module 117 may have any form, such as square, rectangular, round or elliptic, and may be packed into fibers 100 having a wide range of forms and configurations, Introducing fiber modules 117 having an intermediate dimension between cores or core groups and whole fiber 100 (each module 117 may have e.g. tens, hundreds or thousands of cores) enables simpler production and higher flexibility on forming fiber 100 from fiber modules 117. For example, as illustrated in FIG. 2D, rectangular fiber 100 may be assembled from rectangularly arranged square fiber modules 117, e.g., using a package support 118A and a respective attachable cover 118B. Fiber modules 117 may simply be mechanically held by package support 118A and cover 118B at certain regions along fiber 100 and/or fiber modules 117 may be glued together or otherwise attached at least at certain regions. In another example, illustrated in FIG. 2E, fiber modules 117A, 117B may be arranged around void 112. In certain embodiments, fiber modules 117A, 117B may be arranged to differ in their observation angles and/or in optical elements 140 attached at fiber tip 110 (see e.g., below, FIGS. 4A-4D). For example, fiber units 117A may be configured to cover a field of view in front of void 112 (e.g., be inclined inwards or have respective optical elements) while fiber units 117B may be configured to cover a field of view laterally beyond tip 101 (e.g., be inclined outwards or have respective optical elements). For example, non-limiting inclination angles may be 5-20° inwards and 10-50° outwards. Respective packaging or attachment configurations may be applied to fixate fiber modules 117A, 117B in their respective positions and angles. In certain embodiments, the annular arrangement of fiber modules 117A, 117B may be at the fiber's distal end, while fiber modules 117A, 117B may be separated and re-arranged differently at the fiber's proximal end, e.g., into a rectangular form to cover a face of a single rectangular detector. Thus flexibility in production and use is achieved, which enables independent optimization of the spatial distribution of the fiber modules at either end of fiber 100, to enhance both the optical sensing at the distal end as well as the detection and processing at the proximal end.

Figure 3A:
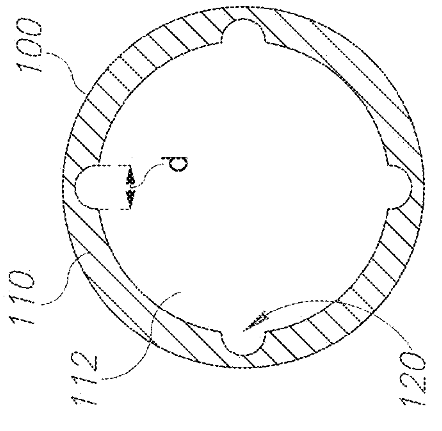
FIGS. 3A-3C are high level schematic cross section illustrations of fibers having working channels and additional channel positions for treatment or illumination fibers, according to some embodiments of the invention.
Figure 3B:
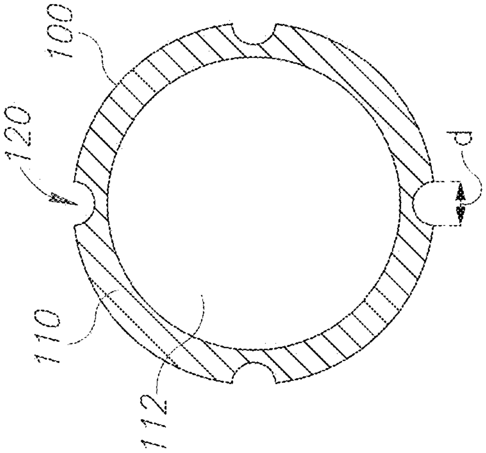
Figure 3C:
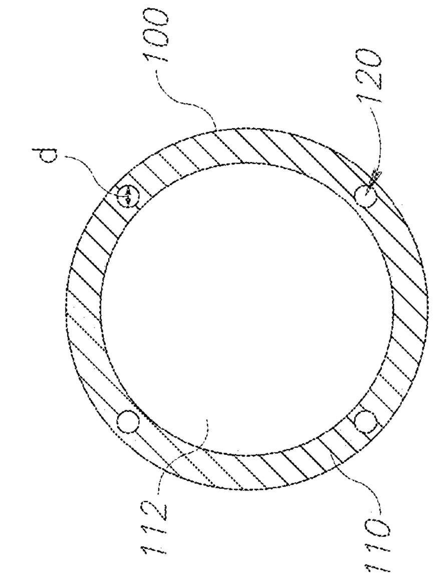

FIGS. 3A-3C are high level schematic cross section illustrations of fiber 100 having working channel 112 and channel positions 120 for treatment or illumination fibers 102, according to some embodiments of the invention. Working channel 112, depicted as void 112 within fiber 100, is surrounded by electromagnetic propagation multicore fiber region 110. Treatment and/or illumination fiber(s) 102 may be integrated into fiber 100 of the endoscope in a way that allows combined imaging and treatment using one fiber, immediate image feedback of the treatment etc. Such combination may be used e.g., as ureteroscope or as any other type of endoscope. In certain embodiments, positioning additional fibers in channels 120 near working channel 112 may be configured to cool down the fibers (e.g., treatment fibers) by the liquids flowing through working channel 112.

In the illustrated examples, treatment or illumination fibers 102 may be inserted at indicated positions 120 (e.g., grooves, or channels), e.g., at an inner wall of multi-core imaging region 110 in fluid communication with working channel 112, e.g., on the periphery of voids 112 (FIG. 3A, channel diameter e.g., ca. 250 μm), at an outer wall of multi-core imaging region 110 in fluid communication with the surroundings of fiber 100, e.g., on the periphery of fiber 100 (FIG. 3B, channel diameter e.g., ca. 250 μm), within multi-core imaging region 110 (FIG. 3C, channel diameter e.g., ca. 200 μm), or combinations of these possibilities. Integration of the treatment or illumination fibers 102 may be carried out before, during or after production of fiber 100. In certain embodiments, glass treatment or illumination fibers 102 may be inserted into grooves 120 after pulling polymer fiber 100.

In certain embodiments, treatment or illumination fibers may be configured and controlled to operate collectively, simultaneously or sequentially, to achieve a desired illumination and/or treatment. For example, the treatment channel may be split into several low power channels 120 to have thinner channels and lower power delivery through each channel. Such configuration may enable increasing the mechanical flexibility of the endoscope, which is very important, e.g., in the field of ureteroscopy. Furthermore, the usage of hollow channels 120 for inserting the external illumination or treatment fibers provides a device configuration exhibiting self-alignment.

Figure 3D:
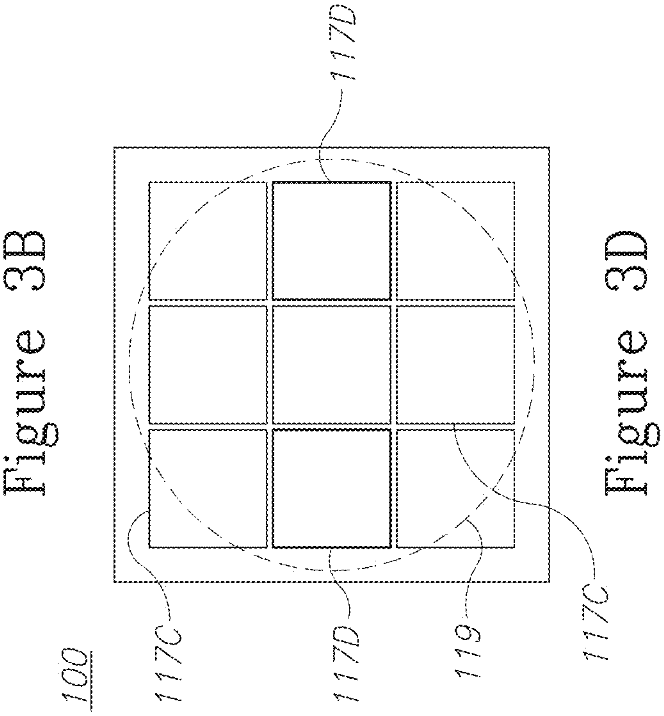
FIG. 3D is a high level schematic illustration of a fiber with an assembled front lens, according to some embodiments of the invention.

FIG. 3D is a high level schematic illustration of fiber 100 with an assembled lens 119, according to some embodiments of the invention. A modular construction of fiber 100 (see e.g., FIGS. 2D, 2E) may be used to modify some of fiber modules 117 to incorporate features into fiber 100 in a simpler manner than incorporating these features into a uniform fiber. fiber modules 117D may be configured in a modular, building block style manner to form various cross sectional organizations with respect to form and functionality of the endoscope. In the illustrated example of certain embodiments, two non-adjacent fiber modules 117D may be coated with a conductor (e.g., a metal) while the rest of fiber modules 117C may be uncoated (and insulating). Such configurations may be used to deliver electricity to fiber tip 101. For example, electromagnetic signals or electromagnetic radiation may be delivered via fiber modules 117D to adjacent tissues or to associated devices or components (e.g., checking equipment or endoscope instrumentation). In the illustrated example, electromagnetic energy may be delivered to distal lens 119 for heating it to prevent fogging upon entry to the body. In certain embodiment, an antenna structure (not shown) may be designed upon lens 119, which receives electromagnetic radiation to heat lens 119 without using contacts. In certain embodiments, radiofrequency (RF) treatment may be applied to tissue or objects surrounding fiber tip 101 via the conductive coating of fiber modules 117D.

Figure 3E:
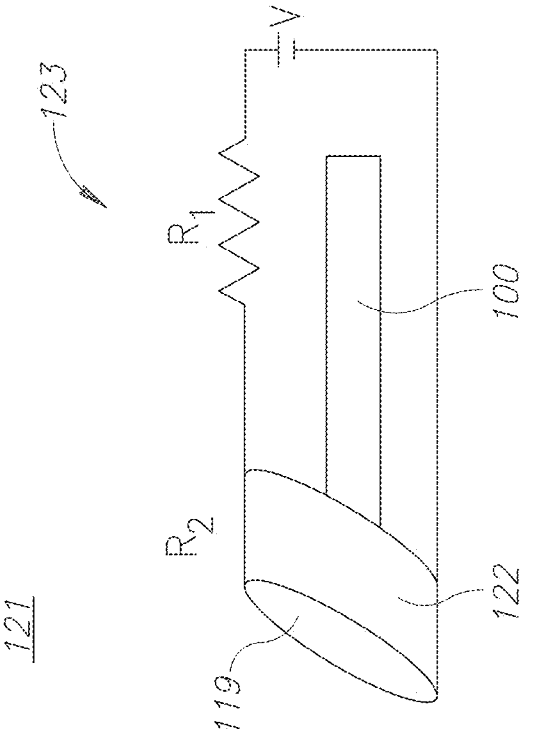
FIGS. 3E-3G are high level schematic illustrations of a defogging mechanism and its effects, according to some embodiments of the invention.
Figure 3F:
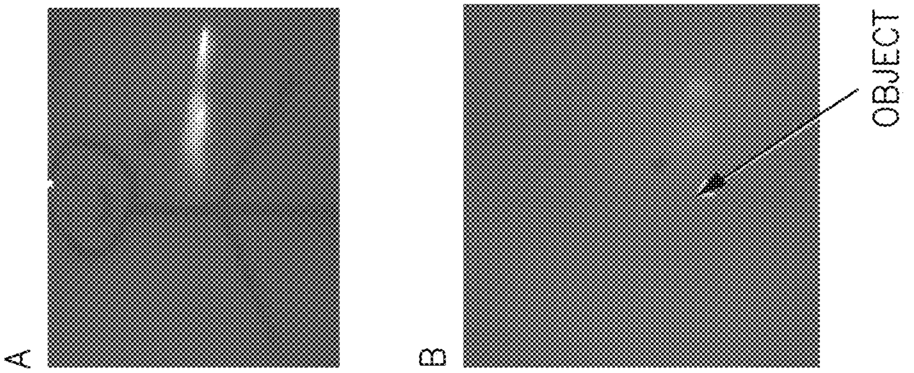
Figure 3G:
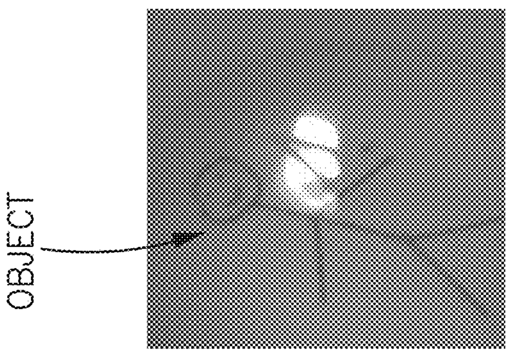

FIGS. 3E-3F are additional high level schematic illustrations of a defogging mechanism 121 and its effects, according to some embodiments of the invention. FIG. 3E illustrates lens 119 coated by a conductive coating 122 connected to an electric circuit 123 configured to heat lens 119 via coating 122, to prevent fog and to defog lens 119 when required. FIG. 3F exemplifies image deterioration by fog accumulation—the top image (A) taken a short time after the beginning of fog accumulation, the bottom image (B) taken later, with the object, marked by an arrow, barely visible. FIG. 3G illustrates the image after defogging—both object and illumination spot are clear again. It is emphasized that as endoscope 105 may be designed to be very thin (e.g., 0.5 mm in diameter) while providing high resolution images, and distal lens 119 may also be ultra-thin. The disclosed defogging mechanism provides effective control of the temperature of lens 119 using a small amount of electrical power, to prevent fogging and overcome an important prior art limitation.

In certain embodiments, endoscope 105 may be operated in the far field (FIG. 1A) or in the near field (FIG. 1B) by properly adapting the focal length of the external optics (the one outside the patient's body, e.g., optical elements 84, 94) to the working distance of treated tissue 70 from the distal tip of the endoscope. Fiber 100 may be configured to deliver full images even with working channel 112 in the middle of the imaging surface by employing far field imaging, e.g., using imaging lens 94 adapted to have a central blocked aperture.

In far field imaging configurations having lens-less fiber tip 101, obtained images may have a number of pixels that is not related to the number of cores 115, enhancing the image resolution with respect to near field embodiments. For example, certain embodiments comprise using as detector 91 an integral imaging sensor capable of sensing wavefront or the 3D topography of inspected tissue 70. In such embodiments, cores 115 may be configured to have a small number of possible spatial modes, resembling the Shack-Hartmann interferometer or a wavefront sensor.

In certain embodiments, cores 115 may be grouped into "super-cores" 116 (see FIG. 2C), each comprising a group of adjacent cores 115. Each "super-core" 116 may be handled as a single wavefront sensing element which delivers information about the wavefront by comparing radiation propagating through individual core members 115 within each "super-core" 116 (or light field sensing. e.g., comparing light directions at different cores operating in near field and multi-mode). The grouping of cores 115 into "super-cores" 116 may be uniform across the face of fiber 100 or be variable, some core groups being larger than others, see e.g., the larger central core group in FIG. 2C).

The grouping of cores 115 may be changed in time according to imaging performance preferences, based e.g., on an even (or uneven) distribution of cores 115 across fiber 110. It is noted that in such configurations a tradeoff exists between depth measurements and resolution. A larger number of cores 115 in each "super-core" 116 provides more details about the three dimensional structure of the imaged region by using more detailed wavefronts, while smaller numbers of cores 115 per group 116 and no grouping at all provide higher resolution. The grouping of cores 115 may hence be designed or modified according to spatially and temporally changing imaging requirements. Complementarily, cores 115 may be handled by processor 170 groupwise with respect to the radiation delivered therethrough, to implement each group 116 as a wavefront sensor. The allocation of cores 115 to core groups 116 may be carried out dynamically, e.g., by processor 170. Additionally, grouping considerations may accompany other considerations regarding imaging performance such as suggested techniques for enhancing resolution and/or depth measurements.

In certain embodiments, near field implementations may comprise sensing the light field between the cores (operating in multi-mode), e.g., measuring directional components of the radiation to yield 3D imaging. Light field sensing may be carried out groupwise with respect to the core grouping.

In certain embodiments, endoscope fiber 100 may comprise multiple cores 115 that are not positioned at equal distances but interspaced unevenly (see FIG. 2A for a schematic illustration). Uneven (irregular) distribution of cores 115 (e.g., a spatial distribution that does not coincide with the spatial distribution of pixels on detector 91) enables, when working in the far-field conditions, to obtain super resolved images since the sampling of cores 115 in the aperture plane Fourier plane) is not uniform and thus the sampling at the aperture plane does not affect the field of view or generate visible limitations in the image plane. The distribution of cores 115 and the interspaces across fiber 100 may be designed to optimize resolution enhancement using algorithmic and optical techniques. Indeed, increasing the distances between cores 115 may provide larger benefits from micro-scanning and application of other super resolution techniques.

In certain embodiments, the optical design of fiber tip 101 may be configured to have working channel 112 positioned asymmetrically and not centrally within the cross section of the tip (not concentric to the imaging channel). The shape of working channel 112 may be configured to different than circular (e.g., elliptic, elongated, polygonal etc.) in order to better encode the optical transfer function (OTF). The working channel shape may be configured to improve inversing the OTF and the algorithmic correcting of the image via the image post processing to yield a super resolved image.

In certain near-field imaging embodiments, an increased depth of focus may be achieved in lens-less embodiments by selecting the best focal positions that can provide the sharpest contrast per each pixel in the generated image, from images captured at different tip positions with respect to tissue 70. The best focus for each pixel may be selected from a plurality of images captured at different tip positions.

In certain embodiments, optical elements 140 may be attached to or produced at distal fiber tip 100 (facing tissue 70). Optical elements 140 may be used to enhance imaging in both far-field imaging and near-field imaging. For example, optical elements 140 may be used to control the field of view, increasing it beyond the edges of tip 101 outwards and/or inwards (in case of a designed working channel void 112).

FIGS. 4A-4D are high level schematic illustrations of hollow endoscope fiber 100 having optical elements 140 at distal tip 101 which compensate for the central void, according to some embodiments of the invention. In embodiments with void(s) 112 at the cross section of fiber 100 at tip 101, various solutions are presented below for imaging a void-facing area 72 in addition to (or in place of) region 71 facing cores 115. It is noted that any type of target 70 may be imaged, e.g., tissue, specific anatomical members, bodily fluids, various stones or obstructions, tumors, foreign bodies etc.

In certain embodiments, illumination source 160 of endoscope 105 and at least some of the optical elements (e.g., tip optical elements 140, proximal optical elements 84, 94) may configured to image at least a part of the area facing void(s) 112 (e.g., void-facing area 72) differently than a rest of the region facing tip 101 (e.g., core-facing region 71). The difference in the imaging may lie in any of polarization, wavelength, wavelength range and/or timing of the illumination. Non-limiting examples are presented in the following.

Figure 4A:
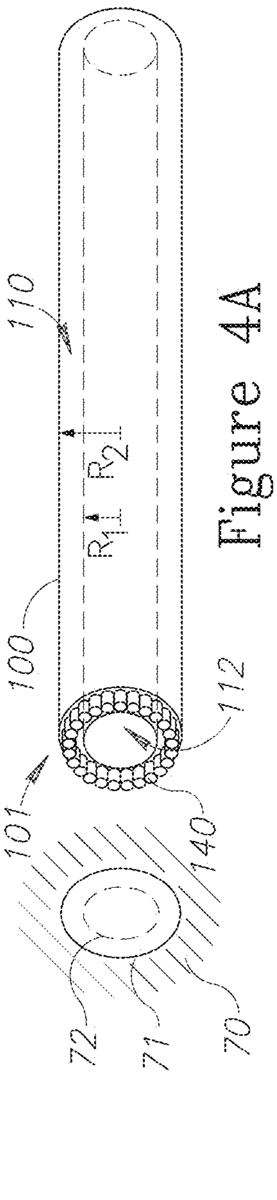
FIGS. 4A-4D are high level schematic illustrations of hollow endoscope fibers having optical elements at the distal tip which compensate for the central void, according to some embodiments of the invention.

Multiple cores 115 may be used to generate a full image, overcoming the lack of cores in hollow region 112 and providing imaging (and illumination) of tissue 70 directly opposite to working channel 112 (void-facing area 72). For example, endoscope 105 may be configured to provide a 90° field of view of fiber 100. FIG. 4A schematically illustrates in a non-limiting manner an annular multicore region 110 (with an inner radius $R_i$ and an outer radius $R_o$) having annularly arranged optical elements 140. Similar principles may be applied to any geometric configuration of fiber tip 100, e.g., any form thereof, any position and form of void(s) 112, etc.

In certain embodiments, optical elements 140 may comprise gradient index (GRIN) lenses cut at specified angles and glued at tip 101 of micro endo scope 105. Each cut GRIN 140 may be cut and positioned to face a different direction in order to enhance the fiber's field of view (FOV) to equal the number of GRINs 140 multiplied by the FOV of each GRIN 140 (or, complementarily or alternatively, enhance the depth of field by configuring some of GRINs 140 to deliver radiation from different depths of field). The cut of the edge of GRIN lenses 140 may realize a prism coupling light into that specific GRIN from different predefined sectors of the field of view. Aspheric lenses may be used as alternative to GRIN lenses as optical elements 140.

Figure 4B:
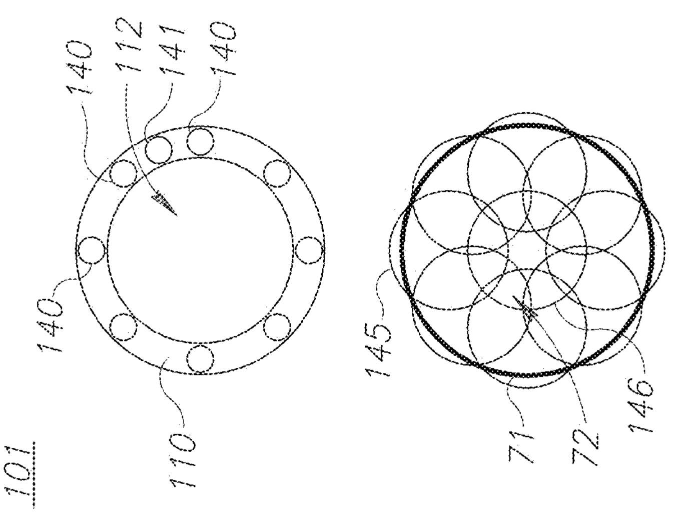
Figure 4C:
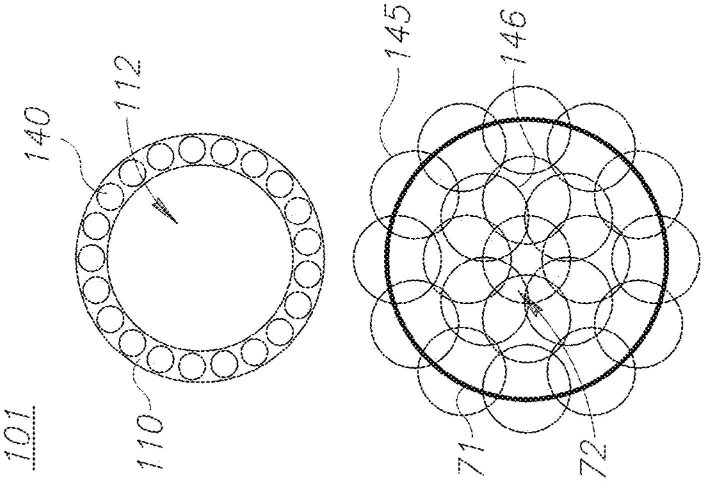
Figure 4D:
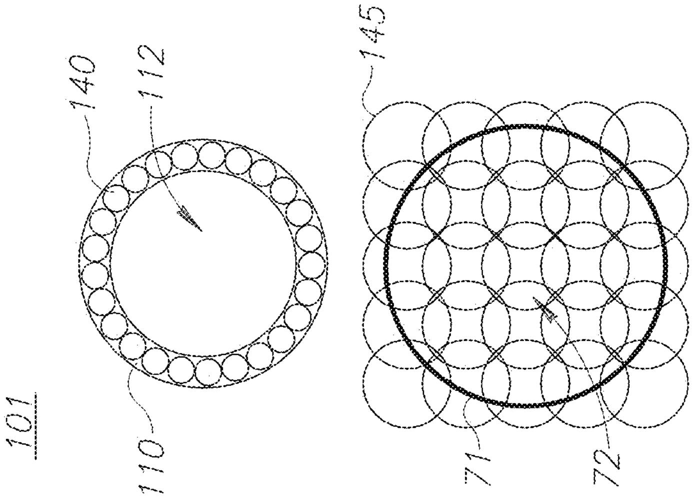

FIGS. 4B-4D schematically illustrates three possible configurations, according to some embodiments of the invention. The large circle schematically represents the periphery of the total FOV of fiber tip 101, which is the boundary of the imaged region facing the cores (71), while the small circles represent the fields of view of individual optical elements 140, 141, taken in a non-limiting illustrative case to be equal. For example, tip FOV (region 71 plus void-facing area 72) may be covered by equally spaced (in FIG. 4B eight) optical elements 140 each imaging a peripheral region 145, and an additional optical element 141 may be configured to image a central region 146. Void-facing area 72 is thus covered centrally by region 146 and its periphery is covered by regions 145. In another example, a larger number (in FIG. 4C twenty one) of optical elements 140 may be configured to have angles covering tip FOV in several concentric circular sets of imaging regions—in the illustrated example twelve peripheral regions 145, eight intermediate regions 146 and one central region. In another example, annularly arranged optical elements 140 (in FIG. 4D twenty five) may be configured to have angles covering the tip FOV in a grid-like manner individual regions 145 partly overlapping and covering tip FOV and possible extending into a larger area. This disclosed method provides high flexibility in adapting fiber tip optical elements 140 to yield a required field of view.

In certain embodiments, optical element 140 may comprise an annular lens coupled to an annular prism that directs light from the whole FOV into the annular lens.

In certain embodiments, possibly without the ring of optical elements described above, the center of FOV may be imaged using selective illumination. Illumination may be directed to the center of FOV and not to its periphery, and accompanying algorithms may be configured to process the detected signals to derive images of the FOV center (e.g., by processor 170).

In certain embodiments, illumination having different polarizations may be used for the central FOV (e.g., void-facing area 72) and for the periphery of FOV (e.g., cores-facing region 71), so that the detected signal is spatially encoded by the difference in polarization, and may be decoded to create images of the whole FOV (see more elaborate explanation below). Optical elements 140 may be birefringent to directly differently polarized illumination to different geometric areas.

In certain embodiments, void 112 may be eccentric or divided into eccentric voids, leaving rooms for ventral cores to image the center of the FOV directly.

In certain embodiments, cores 115 may unequally or non-uniformly spaced within fiber 100, e.g., such that the positions of cores 115 do not coincide with the uniform spatial sampling matrix of the pixels of detector 91 positioned outside the body. The lack of coinciding between the two grids may be utilized to apply geometric super resolving algorithms to improve the quality of the captured image (resembling in a sense the micro-scanning technique).

Certain embodiments may implement micro scanning via the spatial core configuration. For example, fiber 100 may exhibit multicore designs having a low fill factor (the fill factor is the ratio between the core area and the square of the distance between cores, the latter termed pitch). For example, the core diameter may range between 0.4-2.5 μm and the pitch may range between 2-10 μm to yield a range of low fill factors ($1/(\text{pitch}/\text{core diameter})^2$), e.g., fill factors between ¼ and 1/16. When the fill factor is low (e.g., below ¼, below 1/9, e.g., 1/16), simple movement of tip 101 of the micro endoscope (e.g., movement amplitude may equal at least the pitch, e.g. a few microns) enable implementation of the micro-scanning concept to significantly increase the geometric resolution of the device. (It is noted that in case of imaging with large fill factor the micro scanning procedure cannot increase the geometric resolution of the image but rather only to perform over-sampling of the image—because the point spread function (PSF) of the sampling pixel/core itself limits as a spatial low pass the obtainable resolution.) In certain embodiments, spatial scanning methods and temporal scanning methods according to the present disclosure may be combined and adapted to imaging requirements.

In certain embodiments, illumination channel 85 may have time-varying optics which realizes a spatial scanning of the illumination spot. The spatial illumination scanning may be used to construct a wide field image having large field of view which is not affected by the working channel positioned in the center of the tip even if the tip is in near field with respect to the inspected tissue.

In any of the embodiments, processor 170 may be configured to process into images radiation delivered from the imaging region through cores 115 to detector 91 and possibly to implement super-resolution algorithms on the detected radiation.

In certain embodiments, inspected tissue 70 may be illuminated by a tunable laser (e.g., as laser source 64) as illumination source 160. A set of spatial images of tissue 70 may be captured, each image corresponding to a different wavelength. The resulting is hyperspectral image may be used for identification of specific types of tissues (e.g., cancerous tissue) to enhance the imaging. Thus fiber endoscope 105 may provide diagnostic possibilities carried out using different wavelengths (in a specified diagnostic wavelength range, such as infrared wavelengths used to measure hemoglobin oxygenation) that are used for specific purposes and not necessarily for the imaging illumination. For example, multiple narrowband wavelengths 62 may be used to provide diagnostics with one or more wavelength combinations 174 by processor 170. Such combinations may be achieved by using sources with fixed spectral ranges and/or tunable source(s) to change temporally the spectral composition of illumination 85. Examples for diagnostics which may be achieved by wavelength combinations 174 include biopsy (diagnostics of removed tissue) and characterization of biological tissues in situ e.g., by measuring reflectance at different and very specific wavelengths. A non-limiting example includes pulse oximetry which may be extracted by measuring a ratio of absorption at wavelengths of 600-750 nm (e.g., at 660 nm) and 850-1000 nm (e.g., at 910 nm), e.g., as two distinct wavelength (ranges) 62, utilizing the different spectral absorption curves of $HbO_2$ and Hb.

The selection of wavelengths and wavelength bands may be changed during the procedure, manually or automatically, to adapt to different stages in the procedure and different imaging requirements with respect e.g., to spatial or temporal parameters, encountered site and tissue, etc. In one example, single wavelength bands may be illuminated and analyzed separately, to enhance the derived information. Given wavelength bands may be used to illuminate the target from different directions to yield more detailed spatial information.

In certain embodiments, working channel 112 of endoscope 105 configured as an uretero scope may be used to suck out large kidney stones and attach the stones by suction to tip 101 of the endoscope. Treatment laser (possibly incorporated in fiber 100, see FIGS. 3A-3C) may then be used to break the stones while the sucking stabilizes the stones and prevents them from moving around during the medical treatment. Suction may be applied through working channel 112, and the imaging may be used to provide feedback regarding the efficiency of the suction and the treatment. For example, intensive treatment may tend to overcome the suction and release the attached stone. The imaging may be used to detect the development of stone disengagement from fiber tip 101 and to adjust suction and/or applied energy respectively. In this context, splitting of energy application into several fibers as described above may provide more uniform treatment of the stone that employs lower energy concentration at any one point of the stone. Energy application intensity may be regulated at each of the energy sources to avoid stone disengagement from the suction.

In certain embodiments, working channel 112 of the ureteroscope may be used to inject liquid and to slightly change the optical conditions of fiber 100 such that effectively the focal length of lens 140 at tip 101 is changed and focal scanning can be realized to produce the sharpest possible image per each pixel in the image.

Endoscope 105 may be configured as any type of endoscope and be used to handle any type of bodily stones or other obstructions, for example, by laser treatment source 66.

Figure 5A:
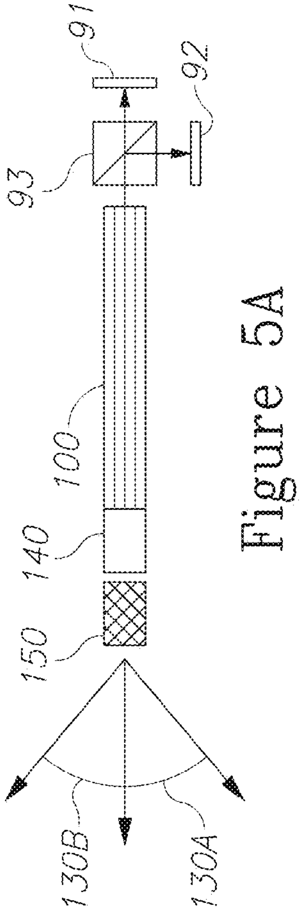
FIGS. 5A-5C are high level schematic illustrations of optical elements, according to some embodiments of the invention.
Figure 5B:
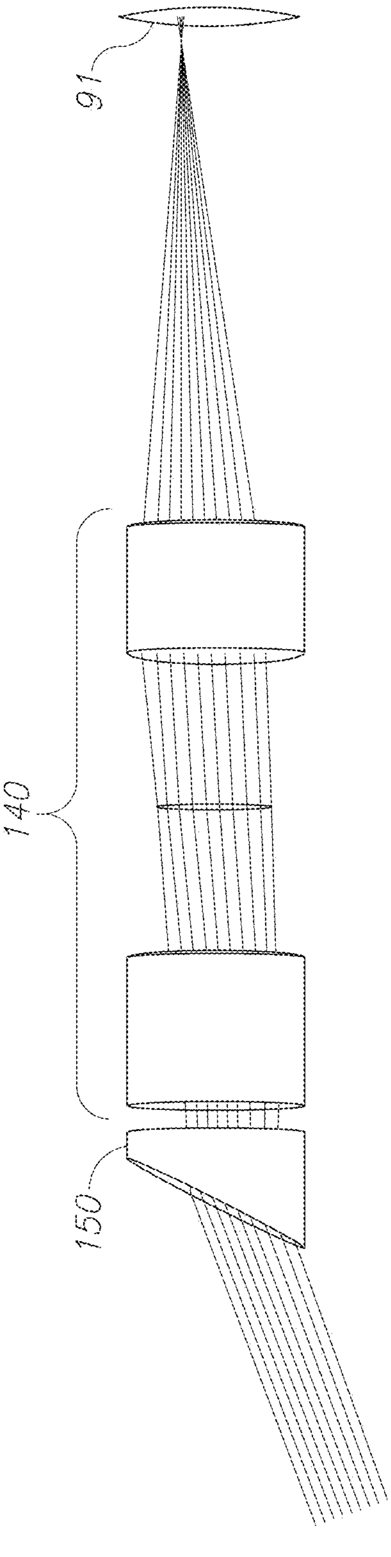
Figure 5C:
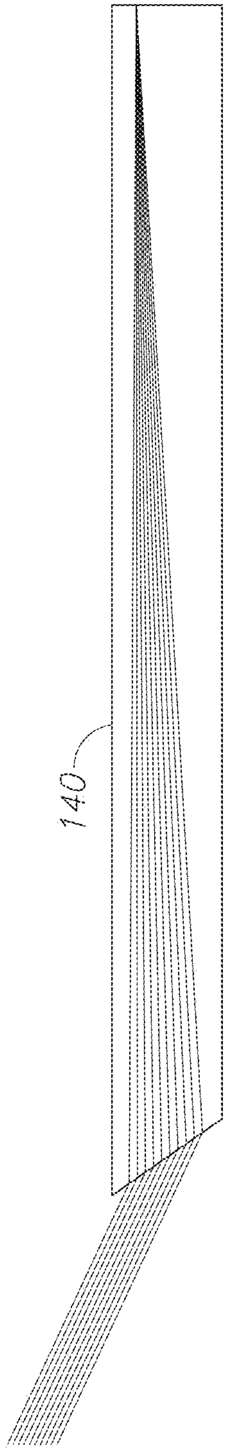

FIGS. 5A-5C are high level schematic illustrations of optical elements 140, according to some embodiments of the invention. In certain embodiments, a polarizing optical element 150 (e.g., a Glan Thompson prism) may be implemented at the end of fiber 100 (FIG. 5A) in addition to imaging lens(es) 140 at tip 101 of the micro-endoscope (e.g., a GRIN lens, aspheric lenses). Polarizing optical element 150 may be configured to increase FOV by polarization multiplexing beyond the limitations of optical element(s) 140. Different fields of view 130A, 130B may be polarization-encoded, folded into endoscope fiber 100 and separated at the output (e.g., using a polarized beam splitter (PBS) 93 before reaching detectors 91, 92). Polarization-encoding may be carried out using different linear polarization directions (e.g. with 45° therebetween), circular polarization etc. Polarization multiplexing may be used to increase the imaged area either laterally or centrally (see above), depending on the configurations of fiber 100 and the optics. Polarization multiplexing may be combined with temporal scanning of the field of view. Polarization multiplexing may be used to enhance three dimensional depth imaging in place or in addition to enlarging the field of view. Different processing algorithms may be applied to the signals of detectors 91, 92 to provide additional information at regions from which both polarization types are detected. Illumination source 160 for polarization multiplexing may be non-polarized (with separation to polarization component being carried out optically), or polarized and have both components.

FIGS. 5B and 5C schematically illustrate embodiments for optical elements 140, 150 at fiber tip 101, namely an angle deflecting element 150 (e.g., a prism) and an imaging optical element 140 (FIG. 5B) and a combined configuration with a faceted GRIN lens 140 (FIG. 5C).

In certain embodiments, certain parts of FOV may be imaged by different optical elements 140 (and respective cores 115) to enable optical triangulation, e.g., distance measurement from tip 101 and the tissue region. Such embodiments allow to trade-off FOV with depth information and thus dynamically allocate imaging resources (e.g., FOV—Field of View, DOF—Depth of Field) according to situation dependent needs. In certain embodiments, different polarizations may be used by different optical elements 140 imaging the same region, so that using polarization enhances depth information instead or in addition to extending the FOV (as explained above). Dynamic variation of polarization may be used to modify the optical performance of fiber 100 during operation. In certain embodiments, different wavelengths may be used by different optical elements 140 imaging the same region, so that using wavelength multiplexing (e.g., using a tunable laser as explained above) enhances depth information instead or in addition to extending the FOV (as explained above).

Dynamic variation of color allocation may be used to modify the optical performance of fiber 100 during operation. For example, multiple laser sources having different wavelengths (e.g., with multiple narrowband wavelengths 62) may be used as illumination source 160, e.g., four channels, three of which used to yield color imaging and the forth used to derive image depth information via triangulation computation. In certain embodiments, the wavelength used for the fourth channel may be identical to the wavelength used in one of the other three channels to facilitate or simplify the triangulation computation.

In certain embodiments, endoscope 105 may be configured to use at least one non-imaged wavelength range, selected to provide additional depth of field or field of view information. In certain embodiments, polarization, wavelength or spatial multiplexing may be used to image a tissue region from different directions, to enable stereoscopic vision of the tissue region. Processor 170 may be configured to derive and provide stereo-imaging.

Moreover, illumination 85 may be improved in quality in different respects, such as its white light spectrum 177 and beam profile 184, as disclosed above.

In certain embodiments, endoscope 105 may be configured to provide two or more levels of resolution, allow balancing field of view information and depth of field information, or allow balance between any other image parameters by adapting the illumination and/or the image processing procedure disclosed herein.

Figure 6A:
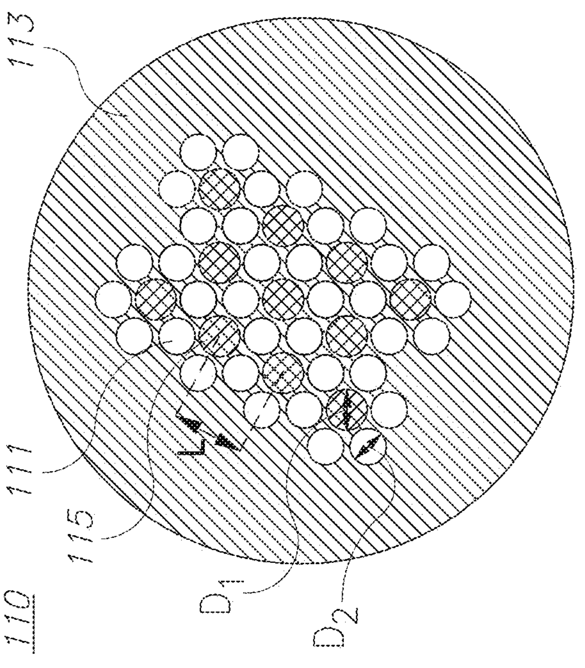
FIGS. 6A and 6B are high level schematic illustration of fiber cross sections with different configurations of the cores, according to some embodiments of the invention.
Figure 6B:
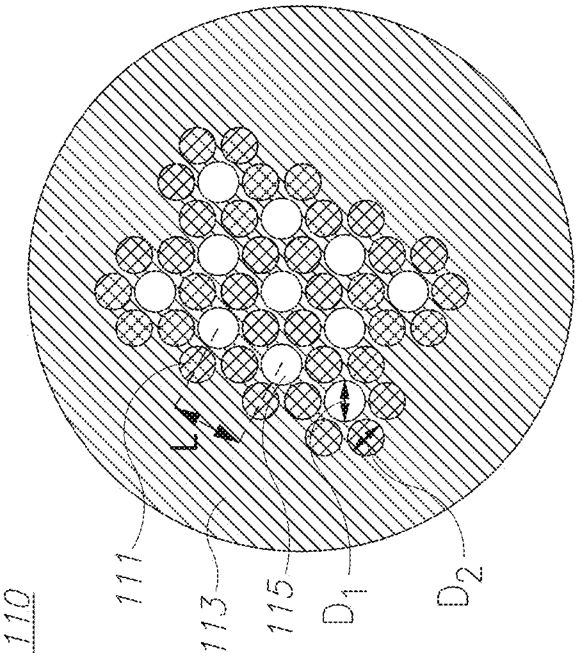
Figure 6C:
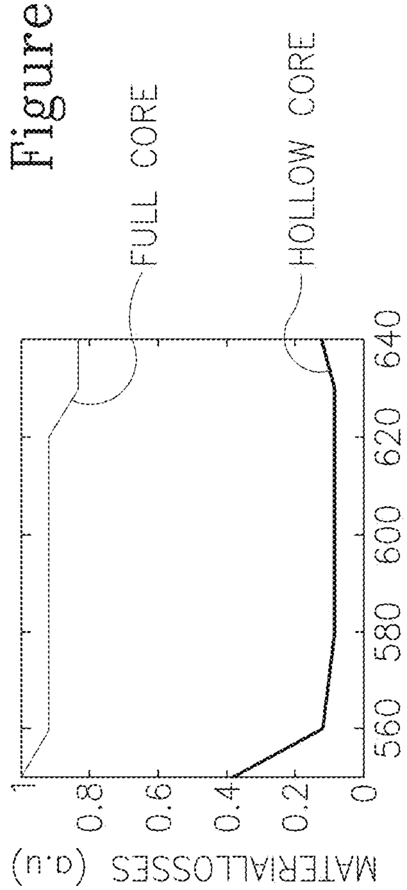
FIG. 6C illustrates comparative experimental results of full core and hollow core fibers, according to some embodiments of the invention.

FIGS. 6A and 6B are high level schematic illustration of fiber cross sections with different configurations of the cores, according to some embodiments of the invention. FIG. 6C illustrates comparative experimental results of full core and hollow core fibers, according to some embodiments of the invention.

The configuration of the cores (dimension, material, interspaces) may be designed to reduce crosstalk between cores 115 and to be less affected by its banding. For example, crosstalk reduction may be achieved in the fabrication process by generating physical barriers between the cores or by using anti-crosstalk layer(s). Core spacing may be selected to reduce crosstalk between adjacent cores 115 below a specified threshold. For example, crosstalk may be reduced by spacing the cores (e.g., by at least 411 between cores) and by increasing the refraction index difference between the cores and the cladding. The cores may be interspaced by structures such as air holes or doped polymer material (e.g., with incorporated nanoparticles). Cores 115 may be hollow, made of polymer material and/or include nanoparticles to control the refractive index. In certain embodiments, contrast may be enhanced by placing the hardware with the external holes array. In certain embodiments, an optical element (e.g., optical element 94) may be added between the output of fiber 100 and the imaging system and configured to block the output coming from cladding 113 thus transferring only the information going out from optical cores 115. The optical element may comprise an intensity mask having a value of one for all core locations and a value of zero for all cladding locations to make all and only information from the cores to propagate to detector 91.

In certain embodiments, the difference in the refraction index between cores 115 and cladding 113 may be designed to be large enough, and/or intermediate elements 111 may be introduced to reduce interaction between radiation propagating in different cores 115. Core 115 and/or cladding 113 and/or elements 111 may comprise polymer with incorporated nanoparticles. Due to plasmonic resonance of the nanoparticles at specific wavelengths an effective increased refraction index may be obtained for the doped material. The specific wavelengths may be selected to be close to wavelength bands (e.g., within a few nm, e.g., ±5 nm at most) of illumination source 160 (e.g., three or four color lasers 62 and/or 64). It is noted that as both the plasmonic resonance and the bandwidth of illumination lasers are narrow, they may be matched to yield an effectively increased refractive index by the nanoparticles at the illumination wavelengths.

In certain embodiments, hollow cores through which no light coupling is obtained may be interlaced as intermediate elements 111 between cores 115 (see FIG. 6A). Hollow cores 111 may be used to reduce the effective refraction index difference between light conducting solid cores 115 and their surrounding medium 113.

In certain embodiments, cores 115 may be hollow (FIG. 6B) and be isolated by doped or non-doped solid polymer. Hollow cores 115 (air holes) were shown to very significantly reduce material losses (FIG. 6C) and are thus exceptionally advantageous when using polymer fibers 100 which are characterized by relatively large losses compared to glass fibers. The main advantage of polymer fibers is their flexibility, enable strong bending which is required under certain endoscope applications (e.g., treating kidney stones as presented above).

Fiber materials (for cladding 113 and intermediate elements 111 if any) and doping may be selected according to the required refractive indices and mechanical properties of fiber 100, and may comprise various types of biocompatible (or not biocompatible, e.g., in non-medical uses) polymers, possibly doped with nanoparticles to influence the refractive indices. Either or both illumination wavelength ranges and types of nanoparticles may be selected to optimize the changes in the refractive indices to optimize the radiation transfer through the cores. In any of the embodiments, core diameter $D_1$, diameter of intermediate elements $D_2$ and distance between cores L may be configured to achieve specified optical performance parameters.

Figure 7:
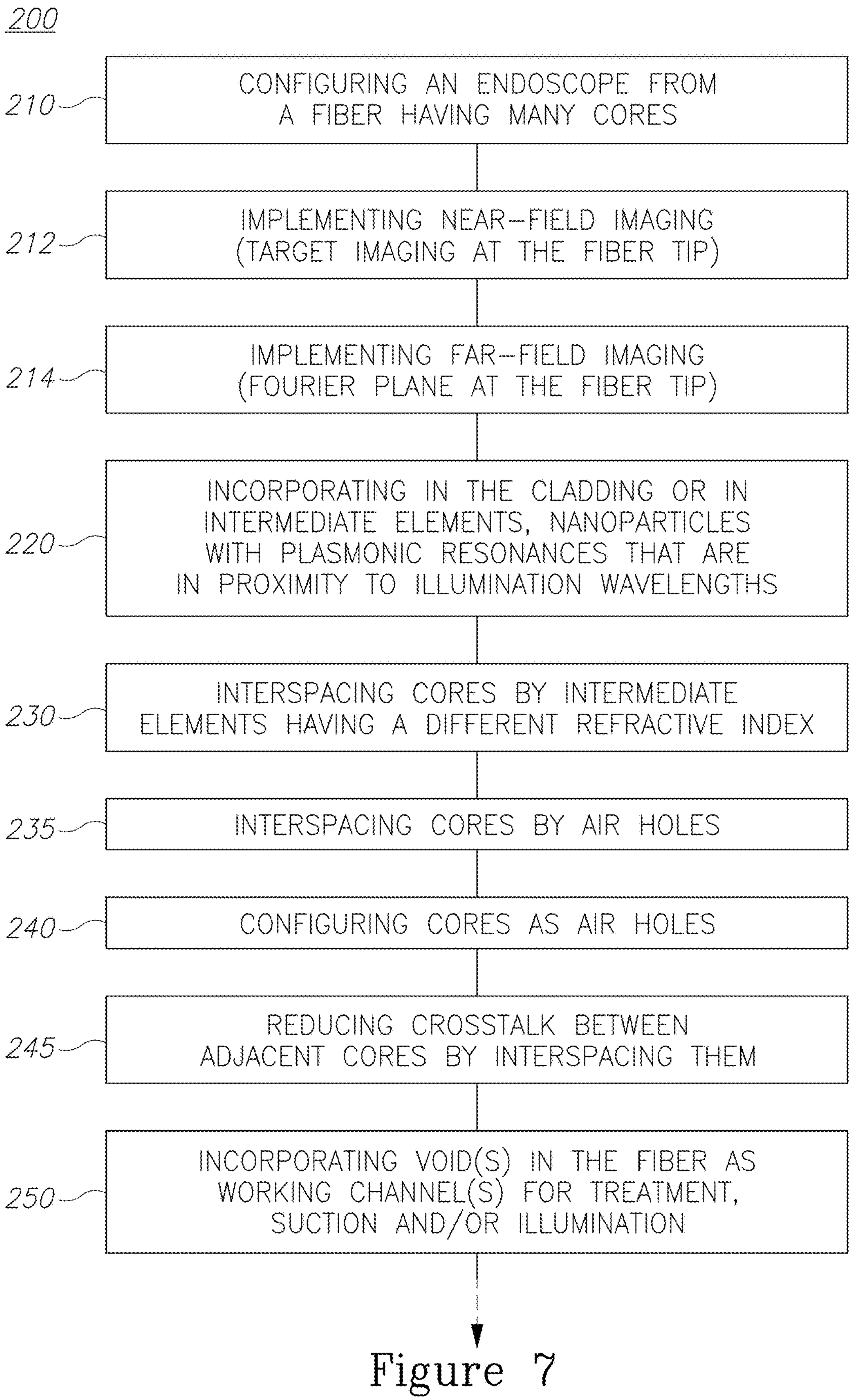
FIG. 7 is a high level schematic flowchart illustrating a method, according to some embodiments of the invention.

FIG. 7 is a high level schematic flowchart illustrating a method 200, according to some embodiments of the invention. Data processing stages and control stages may be implemented by respective processors and algorithms may be implemented by respective computer program product(s) comprising a computer usable medium having computer usable program code tangibly embodied thereon, the computer usable program code configured to carry out at least part of the respective stages.

Method 200 comprises configuring an endoscope from a fiber with at least several hundred cores (stage 210), e.g., having a multi-core imaging region or a multi-core tip configured to deliver reflected illumination along the fiber for an external detector. Method 200 may comprise implementing near-field imaging (target imaging at the fiber tip) (stage 212) and/or implementing far-field imaging (Fourier plane at the fiber tip) (stage 214).

In certain embodiments, method 200 may comprise configuring an endoscope from a plurality of fibers, grouped together, each having at least one hundred cores distributed at a fill factor smaller than ¼, or even below ⅕, and at least one photonic illumination fiber, implementing three dimensional sensing by handling the cores group-wise with respect to radiation delivered therethrough, implementing super-resolved imaging by micro scanning over a pitch distance between the cores, and configuring at least one optical element at a distal tip of the fibers to enhance a field of view and/or a depth of field of the endoscope beyond a region facing a tip of the fibers and congruent thereto.

Method 200 may comprise at least one of the following stages for reducing losses and/or cross talk between cores: incorporating in the cladding, nanoparticles with plasmonic resonances that are in proximity to illumination (and imaging) wavelengths (stage 220); interspacing cores by intermediate elements (possibly incorporating nanoparticles)

having a different refractive index than the cores (stage 230), e.g., by 0.1; interspacing cores by air holes (stage 235) and configuring cores as air holes (stage 240), and may comprise reducing crosstalk between adjacent cores by interspacing them (stage 245).

In certain embodiments, method 200 may further comprise incorporating one or more void(s) in the fiber as working channel(s) for treatment, suction and/or illumination (stage 250).

In certain embodiments, method 200 may further comprise splitting treatment and/or illumination into several fibers operating collectively (stage 260) and/or incorporating additional fibers at the periphery of the fiber or of the void(s) (stage 265). Method 200 may comprise cooling incorporated fibers through the working channel (stage 267). In certain embodiments, method 200 may further comprise controlling treatment and/or suction optically or automatically using optical input during the treatment (stage 270), and treating bodily stones by the endoscope, e.g., kidney stones with an ureteroscope configuration (stage 275).

Method 200 may further comprise using lens-less configurations, without any distal optical elements (stage 277) and/or using distal optical elements to control the field of view, the depth of field, implement image multiplexing and/or determine imaging parameters (stage 282), for example by attaching or producing optical element(s) at the fiber tip (stage 280). Method 200 may comprise enhancing the field of view and/or the depth of field of the endoscope beyond a region facing the tip of the fibers and congruent thereto (stage 285). Method 200 may comprise configuring the optical element(s) to image void-facing areas (stage 290), for example, using a lens with blocked aperture (stage 292); using multiple prisms which optically communicate with the cores (stage 295) and configuring the prisms to image void-facing areas (stage 300), e.g., associating each prism with one or more cores (stage 305); imaging void-facing areas using different polarization, wavelength, wavelength range and/or timing of the illumination (stage 310), in the former using birefringent optical elements for polarization multiplexing (stage 315).

In certain embodiments, method 200 may further comprise implementing super-resolution algorithms (on the detected radiation) to enhance resolution, field of view and/or depth of field (stage 320).

In certain embodiments, method 200 may further comprise reducing speckle patterns by using Barker codes for optimizing coherence modulation (stage 317). Method 200 may further comprise deriving 3D data using structured light illumination and processing (stage 319) and possibly enhancing super resolution processing using the patterned illumination (stage 322) as done, e.g., in time multiplexing super resolving concepts. Method 200 may further comprise beam-shaping the illumination at the distal tip (stage 324).

In certain embodiments, method 200 may further comprise any of: distributing the cores irregularly (with respect to detector pixel order) over the tip cross section (stage 332), distributing the cores at a small fill factor (stage 334), and implementing micro-scanning of the region facing the tip (stage 336). In certain embodiments, method 200 may comprise enhancing images by optimizing pixel focus over different tip positions (stage 338), for example by selecting the best focus for each pixel from a plurality of images captured at different tip positions, and composing an enhanced imaged from the pixels at their selected best focus.

In certain embodiments, method 200 may comprise handling the cores groupwise, possibly with dynamic allocation of cores to groups, to implement wavefront sensing by each group (stage 340). Method 200 may comprise implementing light field sensing. e.g., comparing light directions at different cores operating in near field and multi-mode.

In certain embodiments, method 200 may further comprise using non-imaged wavelengths to provide additional field of view and/or depth of field information (stage 350). Method 200 may comprise collecting diagnostic data using, possibly non-imaged, diagnostic wavelength ranges (stage 360). In any of the embodiments, method 200 may comprise configuring the endoscope as a laparoscope or an ureteroscope (stage 370).

In certain embodiments, method 200 may further comprise configuring the illumination to have multiple narrowband wavelengths (stage 362) and possibly deriving diagnostic data from measurements at different wavelengths (stage 364) and/or enhancing super resolution processing using wavelength multiplexing with respect to the multiple narrowband sources (stage 366). In certain embodiments, method 200 may further comprise providing wideband white illumination using a PCF with zero dispersion point(s) selected to yield spectral broadening (stage 368).

Method 200 may further comprise producing the fiber from standardized fiber modules (stage 380). In certain embodiments, method 200 comprises packaging the fiber modules into desired fiber cross section forms or configurations (stage 382). Method 200 may comprise modifying the spatial relations of the fiber modules along the fiber (stage 385), e.g., to have a circumferential arrangement of fiber modules at the distal tip and a compact arrangement of fiber modules at the proximal tip of the fiber.

In certain embodiments, method 200 may further comprise applying conductive coatings to some fiber modules, with other fiber modules as insulators (stage 387), e.g., for delivering electromagnetic energy to the fiber tip via the conductive coating, e.g., for heating the fiber tip (stage 390), elements associated with the fiber tip and/or a surroundings of the fiber tip. Method 200 may further comprise preventing fog upon and defogging the at least one optical element when required via a heated conductive coating thereof.

Figure 8A:
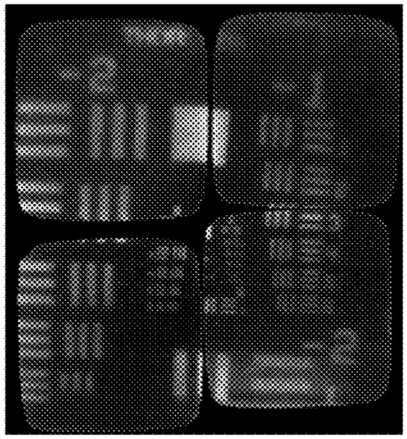
FIGS. 8A-8E are high level schematic illustrations of experimental imaging results for bundled fibers, according to some embodiments of the invention.
Figure 8B:
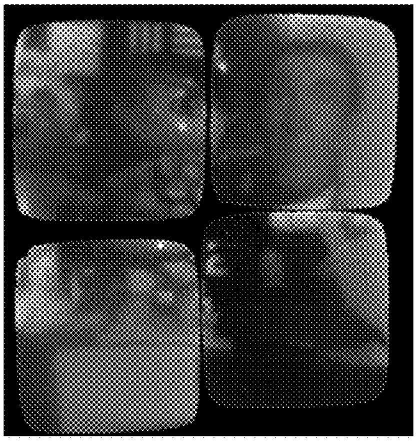
Figure 8C:
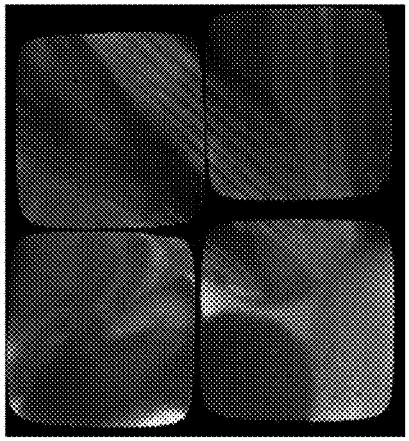
Figure 8D:
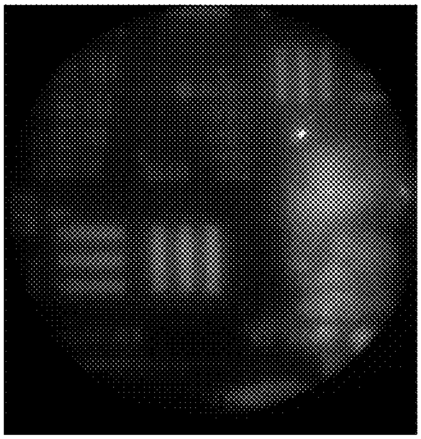
Figure 8E:
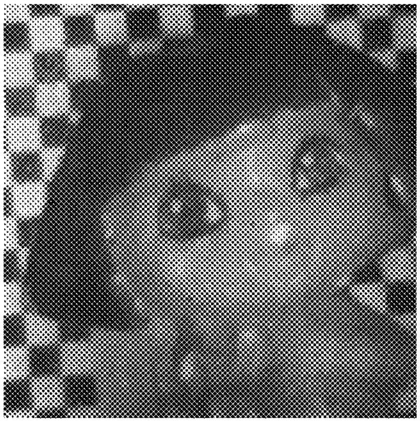

FIGS. 8A-8E are high level schematic illustrations of experimental imaging results for bundled fibers, according to some embodiments of the invention. The imaging configuration is illustrated schematically in FIG. 1B. The presented results represent raw data, prior to the application of the image processing algorithms described above. FIGS. 8A-8C illustrate the imaging of three different targets using a two by two bundled fiber (as evident in the four sub-images, each received from one fiber module, having a side of 450μ and ca. 23,000 cores per fiber module). The targets are respectively a resolution target, characters (person and doll) and an anatomy model. FIG. 8D illustrates imaging by a single multicore fiber, 1.8 mm in diameter having ca. 500,000 cores. Both configurations achieve very high resolution which is unattainable by current fibers. FIG. 8E illustrates a result achieved by applying image enhancement algorithms applied on the captured image.

Figure 9A:
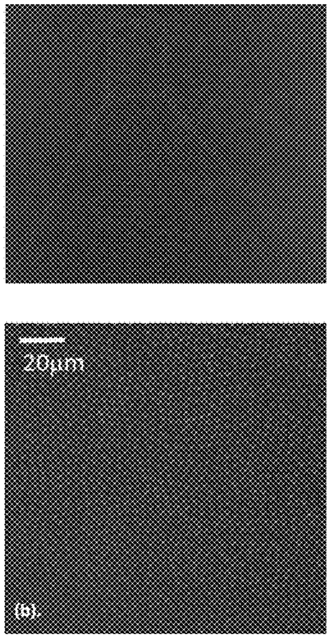
FIGS. 9A-9D are images that provide examples for performance of the endoscope, according to some embodiments of the invention.
Figure 9B:
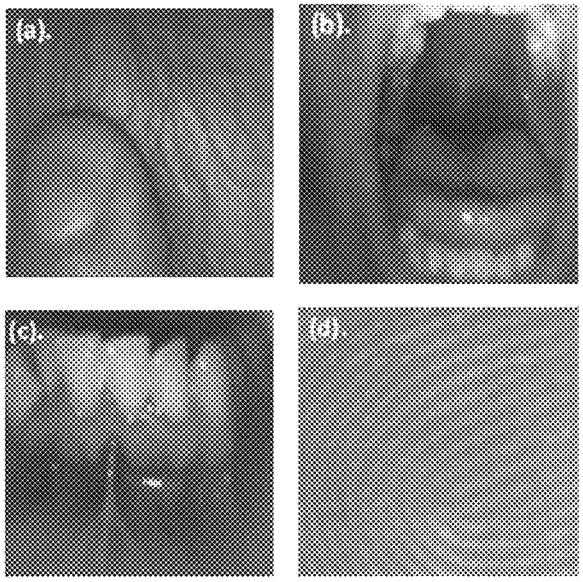
Figure 9C:
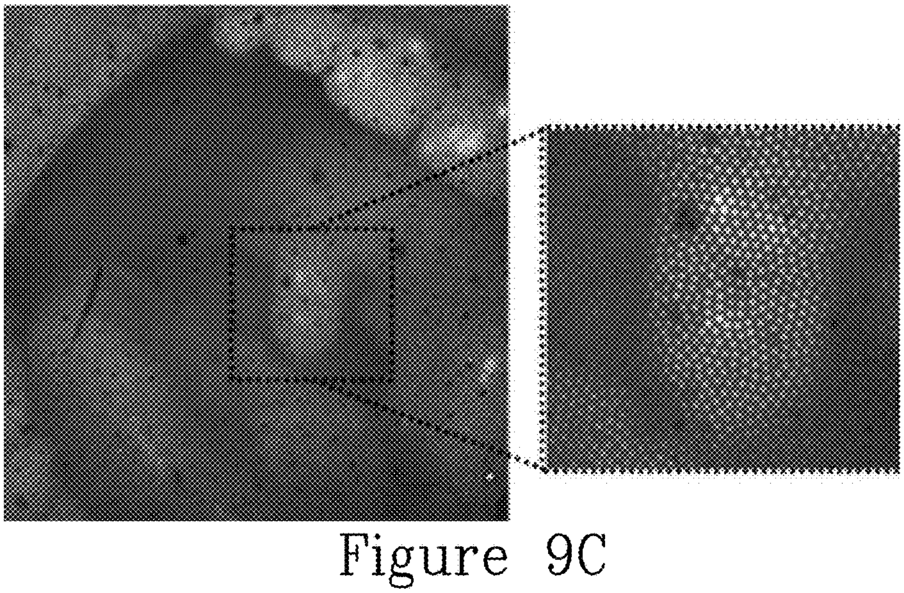
Figure 9D:
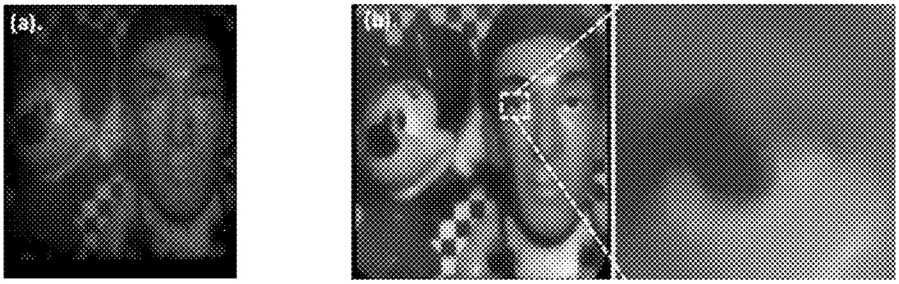

FIGS. 9A-9D are images that provide examples for performance of endo scope 105, according to some embodiments of the invention. FIG. 9A illustrates an example for the multicore configuration of fiber 100, in the illustrated non-limiting case, fiber 100 has an external diameter of 0.45 mm and includes more than 80,000 cores as well as an integrated illumination channel. The bottom image is a magnified view of the marked section in the top image. FIG. 9B illustrates image examples by endoscope 105 of a fingernail (a), a mouth (b), teeth (c) and a fingertip (d). These images were taken using fiber 100 with external diameter of 0.45 mm that includes more than 80,000 cores, and were processed as disclosed above. FIGS. 9C and 9D illustrate examples for processing steps, namely the removal of artifacts and core traces (shown in FIG. 9C) and the improvement of resolution and magnification (examples for the quality improvement of the results is shown in FIG. 9D). For example, disclosed image processing algorithms provide the cleaned image of FIG. 9D at a resolution of 300,000 pixels. Advantageously, the images obtained from multicore fibers 100 are steady and are not influences by fiber bending, outperforming prior art multimode fibers. Advantageously, very thin endoscope 105 provides high resolution medical imaging combined with high maneuverability and compliance with many medical situations.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has been described, but by the appended claims and their legal equivalents.

The invention claimed is:

1. An endoscope comprising:

a fiber comprising at least one fiber module that comprises a plurality of cores;

one or a plurality of optical elements attached at a tip of the fiber; and an illumination source comprising one or a plurality of lasers for multiple narrowband wavelengths, a coherence modulator, one or more photonic crystal fiber, structured light pattern illumination and a laser treatment source, the illumination source configured to provide through illumination channels of the fiber illumination onto a field of view of the at least one fiber module, wherein said one or a plurality of optical elements is configured to cause the illumination to increase the field of view.

2. The endoscope of claim 1, wherein the at least one fiber module comprises a at least one hundred cores distributed at a fill factor smaller than ¼, and wherein the fiber is made of at least one polymer.

3. The endoscope of claim 1, wherein said one or a plurality of optical elements is configured to perform temporal scanning of the field of view.

4. The endoscope of claim 3, wherein said one of a plurality of optical elements comprises a polarizing optical element.

5. The endoscope of claim 4, wherein the polarizing optical element is configured to combine polarization multiplexing with the temporal scanning.

6. The endoscope of claim 5, wherein the polarizing optical element is configured to combine polarization multiplexing that is configured to increase an imaged area laterally or centrally.

7. The endoscope of claim 4, configured to polarization-encode different parts of the field of view, and separate the different parts of the field of view at an output of the fiber.

8. The endoscope of claim 7, further comprising a beam splitter to separate the different parts of the field of view at the output of the fiber.

9. The endoscope of claim 7, wherein the endoscope is configured to polarization encode using one of different linear polarization directions and circular polarization.

10. The endoscope of claim 4, configured to image different parts of the field of view using different optical elements of said one or a plurality of optical elements.

11. The endoscope of claim 10, wherein the endoscope is configured to perform optical triangulation.

12. The endoscope of claim 11, wherein the endoscope is configured to perform optical triangulation to measure a distance between a tip of the endoscope and an imaged tissue.

13. The endoscope of claim 4, configured to employ different polarizations by different optical elements of said one or a plurality of optical elements to image a same region of the field of view.

14. The endoscope of claim 4, wherein the polarizing optical element is configured to dynamically vary polarization in order to modify optical performance of the endoscope.

15. The endoscope of claim 1, wherein the illumination source is configured to dynamically vary color allocation to modify optical performance of the endoscope.

16. The endoscope of claim 15, wherein the illumination source comprises a plurality of laser sources illuminating in different wavelengths.

* * * * *